(12) United States Patent
Smetona et al.

(10) Patent No.: US 10,099,944 B2
(45) Date of Patent: Oct. 16, 2018

(54) ULTRAVIOLET TRANSPARENT ENCLOSURE

(71) Applicant: Sensor Electronic Technology, Inc., Columbia, SC (US)

(72) Inventors: Saulius Smetona, Concord, NC (US); Timothy James Bettles, Columbia, SC (US); Alexander Dobrinsky, Loudonville, NY (US); Michael Shur, Latham, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 92 days.

(21) Appl. No.: 15/388,330

(22) Filed: Dec. 22, 2016

(65) Prior Publication Data

US 2017/0101328 A1    Apr. 13, 2017

Related U.S. Application Data

(63) Continuation-in-part of application No. 14/729,236, filed on Jun. 3, 2015.

(60) Provisional application No. 62/007,141, filed on Jun. 3, 2014.

(51) Int. Cl.
*C02F 1/32* (2006.01)
*A61L 2/10* (2006.01)

(52) U.S. Cl.
CPC ............. *C02F 1/325* (2013.01); *A61L 2/10* (2013.01); *C02F 2201/328* (2013.01); *C02F 2201/3221* (2013.01); *C02F 2201/3222* (2013.01); *C02F 2201/3227* (2013.01); *C02F 2201/3228* (2013.01); *C02F 2303/04* (2013.01)

(58) Field of Classification Search
USPC ..... 250/435, 432 R, 454.11, 455.11; 422/22, 422/24, 186.3
See application file for complete search history.

(56) References Cited

U.S. PATENT DOCUMENTS

| 4,766,321 A | 8/1988 | Lew et al. |
|---|---|---|
| 6,464,936 B1 | 10/2002 | Mowat et al. |
| 6,586,172 B1 | 7/2003 | Gunn et al. |

(Continued)

FOREIGN PATENT DOCUMENTS

| GB | 1017242 A | 1/1966 |
|---|---|---|
| JP | 2010006775 A | 1/2010 |
| TW | 436303 B | 5/2001 |

OTHER PUBLICATIONS

Nguyen, K., U.S. Appl. No. 14/729,236, Non-Final Rejection1, dated Dec. 15, 2016, 17 pages.

(Continued)

*Primary Examiner* — Kiet T Nguyen
(74) *Attorney, Agent, or Firm* — LaBatt, LLC

(57) ABSTRACT

A solution for disinfecting a fluid, colloid, mixture, and/or the like using ultraviolet radiation is provided. An ultraviolet transparent enclosure can include an inlet and an outlet for a flow of media to be disinfected. The ultraviolet transparent enclosure includes a material that is configured to prevent biofouling within the ultraviolet transparent enclosure. A set of ultraviolet radiation sources are located adjacent to the ultraviolet transparent enclosure and are configured to generate ultraviolet radiation towards the ultraviolet transparent enclosure.

20 Claims, 16 Drawing Sheets

(56) References Cited

U.S. PATENT DOCUMENTS

| | | |
|---|---|---|
| 6,773,608 B1 | 8/2004 | Hallett et al. |
| 9,718,706 B2 | 8/2017 | Smetona et al. |
| 2006/0207431 A1 | 9/2006 | Baca et al. |
| 2006/0270960 A1 | 11/2006 | Karp |
| 2013/0236353 A1 | 9/2013 | Blechschmidt et al. |
| 2014/0346370 A1 | 11/2014 | Dobrinsky et al. |
| 2015/0069265 A1 | 3/2015 | Smetona et al. |
| 2015/0136671 A1 | 5/2015 | Barnes |
| 2015/0250907 A1 | 9/2015 | Bilenko et al. |
| 2015/0314024 A1 | 11/2015 | Khan et al. |
| 2017/0100494 A1* | 4/2017 | Dobrinsky ................ A61L 2/10 |

OTHER PUBLICATIONS

Nguyen, K., U.S. Appl. No. 15/662,687, Office Action1, dated Jan. 2, 2018, 14 pages.
Nguyen, K., U.S. Appl. No. 14/729,236, Notice of Allowance, dated Mar. 30, 2017, 5 pages.
Nguyen, K., U.S. Appl. No. 15/662,687, Notice of Allowance, dated May 23, 2018, 5 pages.
Zhou, K., Chinese Application No. 201510301012.2, Office Action1, (With English translation), dated Jun. 12, 2018, 15 pages.

\* cited by examiner

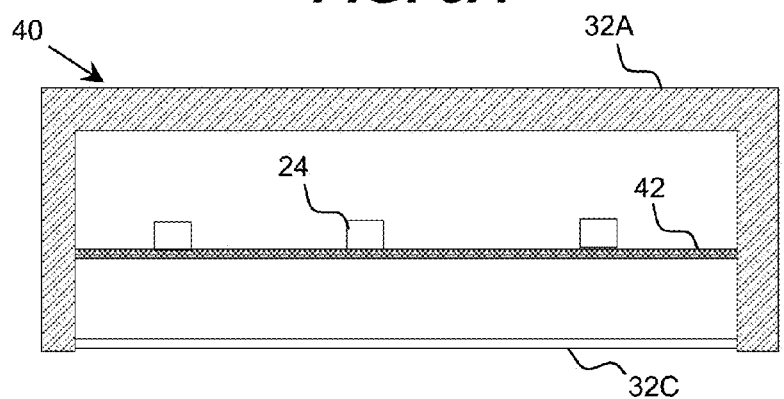
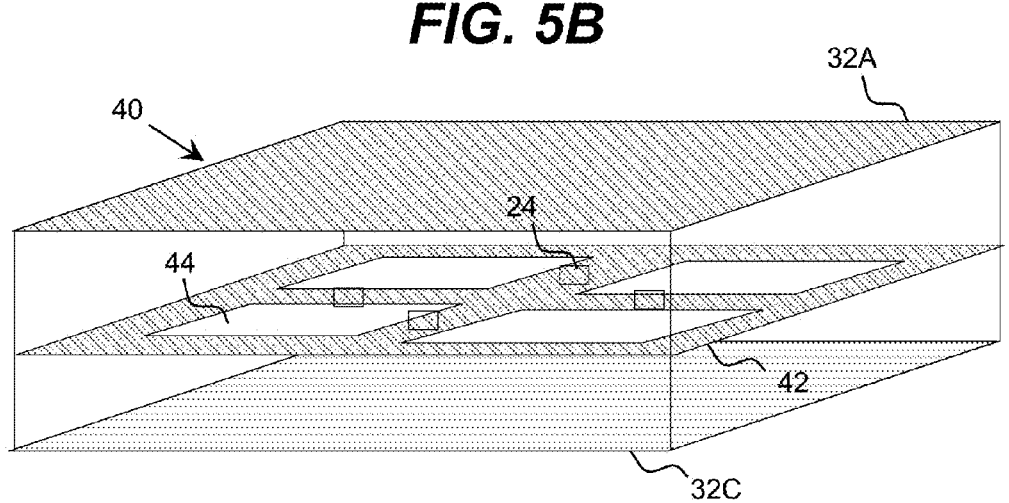

ULTRAVIOLET TRANSPARENT ENCLOSURE

REFERENCE TO RELATED APPLICATIONS

The present patent application is a continuation-in-part application of U.S. application Ser. No. 14/729,236, which was filed on 3 Jun. 2015, which claims the benefit of U.S. Provisional Application No. 62/007,141, titled "UV Transparent Disinfection Enclosure and Device Containing the Same," which was filed on 3 Jun. 2014, both of which are hereby incorporated by reference. Aspects of the invention are related to U.S. patent application Ser. No. 14/478,266, titled "Ultraviolet Diffusive Illumination," which was filed on 5 Sep. 2014, and U.S. patent application Ser. No. 14/640,051, titled "Ultraviolet Surface Illuminator," which was filed on 6 Mar. 2015, both of which are hereby incorporated by reference.

TECHNICAL FIELD

The disclosure relates generally to disinfection, and more particularly, to a solution for disinfecting a fluid, colloid, mixture, and/or the like using ultraviolet radiation.

BACKGROUND ART

Ultraviolet (UV) radiation emitters can be effectively used to disinfect liquids, such as water, and have been utilized in various water treatment facilities. Water treatment using UV radiation offers many advantages over other forms of water treatment, such as chemical treatment. For example, treatment with UV radiation does not introduce additional chemicals or biological contaminants into the water. Furthermore, ultraviolet radiation provides one of the most efficient approaches to water contamination since there are no microorganisms known to be resistant to ultraviolet radiation, unlike other decontamination methods, such as chlorination. UV radiation is known to be highly effective against bacteria, viruses, algae, molds, and yeasts. For example, the hepatitis virus has been shown to survive for considerable periods of time in the presence of chlorine, but is readily eliminated by UV radiation treatment. The removal efficiency of UV radiation for most microbiological contaminants, such as bacteria and viruses, generally exceeds 99%. To this extent, UV radiation is highly efficient at eliminating *E-coli, Salmonella*, Typhoid fever, Cholera, Tuberculosis, Influenza Virus, Polio Virus, and Hepatitis A Virus.

UV radiation disinfection using mercury based lamps is a well-established technology. In general, a system for treating water using ultraviolet radiation is relatively easy to install and maintain in a plumbing or septic system. Use of UV radiation in such systems does not affect the overall system. However, it is often desirable to combine an ultraviolet purification system with another form of filtration since the UV radiation cannot neutralize chorine, heavy metals, and other chemical contaminants that may be present in the water. Various membrane filters for sediment filtration, granular activated carbon filtering, reverse osmosis, and/or the like, can be used as a filtering device to reduce the presence of chemicals and other inorganic contaminants.

Mercury lamp-based ultraviolet radiation disinfection has several shortcomings when compared to deep ultraviolet (DUV) light emitting device (LED)-based technology, particularly with respect to certain disinfection applications. For example, in rural and/or off-grid locations, it is desirable for an ultraviolet purification system to have one or more of various attributes such as: a long operating lifetime, containing no hazardous components, not readily susceptible to damage, requiring minimal operational skills, not requiring special disposal procedures, capable of operating on local intermittent electrical power, and/or the like. Use of a DUV LED-based solution can provide a solution that improves one or more of these attributes as compared to a mercury vapor lamp-based approach. For example, in comparison to mercury vapor lamps, DUV LEDS have substantially longer operating lifetimes (e.g., by a factor of ten), do not include hazardous components (e.g., mercury), which require special disposal and maintenance, are more durable in transit and handling (e.g., no filaments or glass), have a faster startup time, have a low operational voltage, are less sensitive to power supply intermittency, are more compact and portable, can be used in moving devices, can be powered by photovoltaic (PV) technology, which can be installed in rural locations having no continuous access to electricity and having scarce resources of clean water, and/or the like.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the invention provide a solution for disinfecting a fluid, colloid, mixture, an article, an object, an extremity and/or the like using ultraviolet radiation. In one embodiment, an ultraviolet transparent enclosure can include an inlet and an outlet for a flow of media to be disinfected. The ultraviolet transparent enclosure includes a material that is configured to prevent biofouling within the ultraviolet transparent enclosure. A set of ultraviolet radiation sources are located adjacent to the ultraviolet transparent enclosure and are configured to generate ultraviolet radiation towards the ultraviolet transparent enclosure.

A first aspect of the invention provides an apparatus comprising: an ultraviolet transparent enclosure including an inlet to receive a flow of media entering the ultraviolet transparent enclosure for disinfection and an outlet to supply the flow of media from the ultraviolet transparent enclosure after disinfection, wherein the ultraviolet transparent enclosure includes a plurality of spaced media separators, each contacting only one side surface of the ultraviolet transparent enclosure, wherein adjacent media separators each contact an opposing side surface, the plurality of spaced media separators forming a channel that twists and turns the flow of media from the inlet to the outlet, and wherein the ultraviolet transparent enclosure includes a material that prevents biofouling from accumulating therein; and a set of ultraviolet radiation sources, located adjacent to the ultraviolet transparent enclosure, to generate ultraviolet radiation towards the ultraviolet transparent enclosure.

A second aspect of the invention provides an apparatus comprising: an ultraviolet transparent enclosure including an inlet to receive a flow of media entering the ultraviolet transparent enclosure for disinfection and an outlet to supply the flow of media from the ultraviolet transparent enclosure after disinfection, wherein the ultraviolet transparent enclosure includes a material that prevents biofouling from accumulating therein; a reflective enclosure that encases the ultraviolet transparent enclosure; and an illuminator integrated within an inner surface of the reflective enclosure, wherein the illuminator comprises a set of ultraviolet radiation sources positioned to generate ultraviolet radiation towards the ultraviolet transparent enclosure.

A third aspect of the invention provides a system comprising: an ultraviolet transparent enclosure including an inlet and an outlet for a flow of media to be disinfected, wherein the ultraviolet transparent enclosure includes a material having a laminate of sublayers that are configured to prevent biofouling within the ultraviolet transparent enclosure; and a set of ultraviolet radiation sources located adjacent to the ultraviolet transparent enclosure, the set of ultraviolet radiation sources configured to generate ultraviolet radiation towards the ultraviolet transparent enclosure.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 5A and 5B show assemblies of UV radiation sources for diffusively emitting UV radiation according to embodiments of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1A:
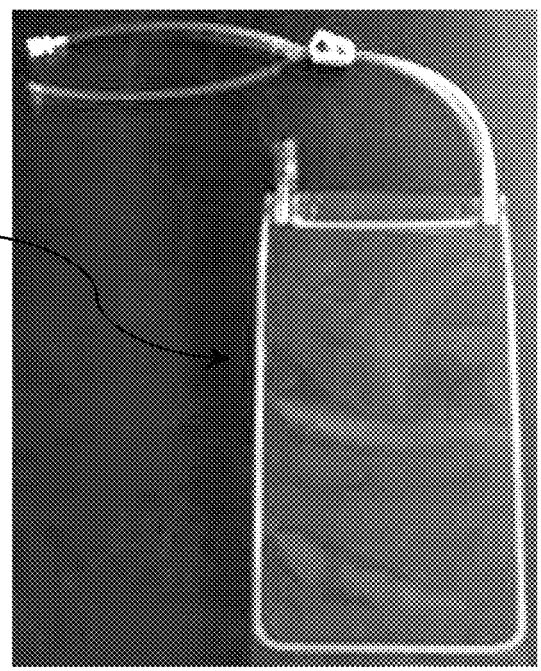
FIGS. 1A and 1B show illustrative ultraviolet transparent enclosures according to embodiments of the invention.

As indicated above, aspects of the invention provide a solution for disinfecting a fluid, colloid, mixture, an article, an object, an extremity and/or the like using ultraviolet radiation. In one embodiment, an ultraviolet transparent enclosure can include an inlet and an outlet for a flow of media to be disinfected. The ultraviolet transparent enclosure includes a material that is configured to prevent biofouling within the ultraviolet transparent enclosure. A set of ultraviolet radiation sources are located adjacent to the ultraviolet transparent enclosure and are configured to generate ultraviolet radiation towards the ultraviolet transparent enclosure.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

As used herein, unless otherwise noted, the term "set" means one or more (i.e., at least one) and the phrase "any solution" means any now known or later developed solution. As also used herein, a layer is a transparent layer when the layer allows at least ten percent of radiation having a target wavelength, which is radiated at a normal incidence to an interface of the layer, to pass there through. Furthermore, as used herein, a layer is a reflective layer when the layer reflects at least ten percent of radiation having a target wavelength, which is radiated at a normal incidence to an interface of the layer. In an embodiment, the target wavelength of the radiation corresponds to a wavelength of radiation emitted or sensed (e.g., peak wavelength +/–five nanometers) by an active region of an optoelectronic device during operation of the device. For a given layer, the wavelength can be measured in a material of consideration and can depend on a refractive index of the material. It is understood that, unless otherwise specified, each value is approximate and each range of values included herein is inclusive of the end values defining the range.

As used herein, the term "disinfection" and its related terms means treating a medium so that the medium includes a sufficiently low number of contaminants (e.g., chemical) and microorganisms (e.g., virus, bacteria, and/or the like) so that the medium can be utilized as part of a desired human interaction with no or no reasonable risk for the transmission of a disease or other harm to the human. For example, disinfection of the medium means that the medium has a sufficiently low level of active microorganisms and/or concentration of other contaminants that a typical human can interact with the medium without suffering adverse effects from the microorganisms and/or contaminants present on or in the medium. In addition, disinfection can include sterilization. As used herein, the term "sterilization" and its related terms means neutralizing an ability of a microorganism to reproduce, which may be accomplished without physically destroying the microorganism. In this example, a level of microorganisms present on the item cannot increase to a dangerous level and will eventually be reduced, since the replication ability has been neutralized. A target level of microorganisms and/or contaminants can be defined, for example, by a standards setting organization, such as a governmental organization.

Figure 1B:
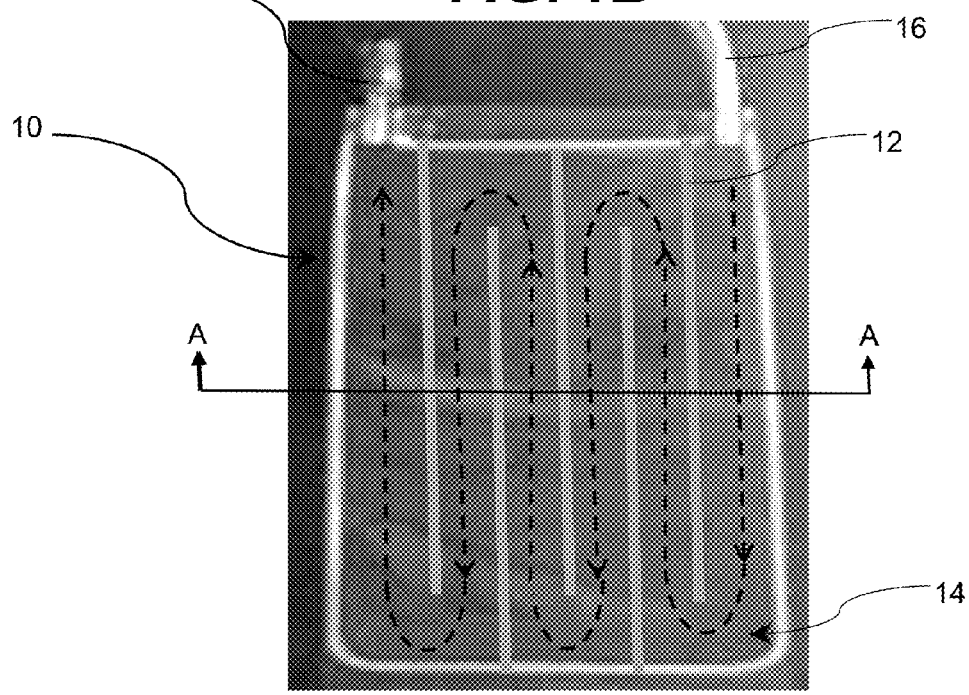
Figure 2A:
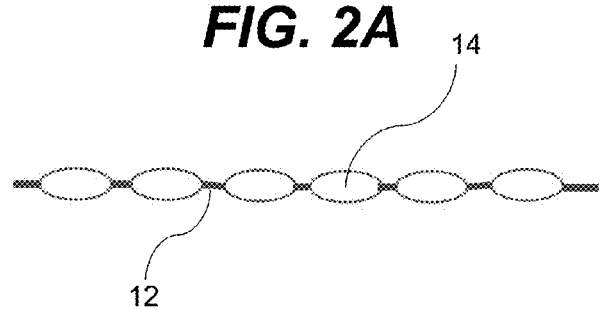
FIG. 2A shows a cross sectional view of an illustrative ultraviolet transparent enclosure and FIG. 2B shows a cross sectional view of an illustrative disinfection system according to embodiments of the invention.

Turning to the drawings, FIGS. 1A and 1B show illustrative ultraviolet transparent enclosures according to embodiments of the invention. In FIG. 1A, the ultraviolet transparent enclosure 10 is shown as a flexible ultraviolet transparent bag. As shown in FIG. 1B, the ultraviolet transparent enclosure 10 can include a plurality of welded separators 12 for creating a channel 14 through which a fluid, colloid, mixture, and/or the like can flow (e.g., a serpentine channel as shown by the dotted arrows through the channel 14). The placement of the welded separators 12 within the ultraviolet transparent enclosure 10 is determined by the location of an inlet 16 and an outlet 18 to the ultraviolet transparent enclosure 10 and controls the flow of the fluid, colloid, mixture, and/or the like. Although only one inlet 16 and one outlet 18 is shown, it is understood that the enclosure 10 can include any number of inlets and outlets. Turning now to FIG. 2A, a cross sectional view along line A-A of the enclosure 10 in FIG. 1B is shown, where the segments of the channel 14 are created by the welded separators 12.

The ultraviolet transparent enclosure 10 can include a material that is a low-to-none biofouling material, such as a UV transparent polymer (e.g., fluorinated ethylene propylene (FEP), tetrafluoroethylene hexafluoropropylene vinylidene fluoride (THV), polytetrafluoroethylene (PTFE), and/or the like), and/or the like. The low-to-none biofouling material prevents the accumulation of microorganisms, algae, plants, and/or the like, within the enclosure 10. Also, the material of the enclosure 10 can be chemically inert to any interaction with the disinfection media (e.g., fluid, colloid, mixture, and/or the like), and can be chemically stable to exposure to UV radiation described herein. In an embodiment, the ultraviolet transparent enclosure 10 includes a transparency of at least 50% to the surface normal UV light. The material of the welded separators 12 can include a similar material. A method of forming the ultraviolet transparent enclosure 10 with the welded separators 12 can include: selecting a UV transparent polymer material for the ultraviolet transparent enclosure 10 and the welded separators 12; determining the melting temperature of the UV transparent polymer; and applying pressure and temperature comparable to the melting temperature at regions of the enclosure 10 that require the welded separators 12.

Figure 3:
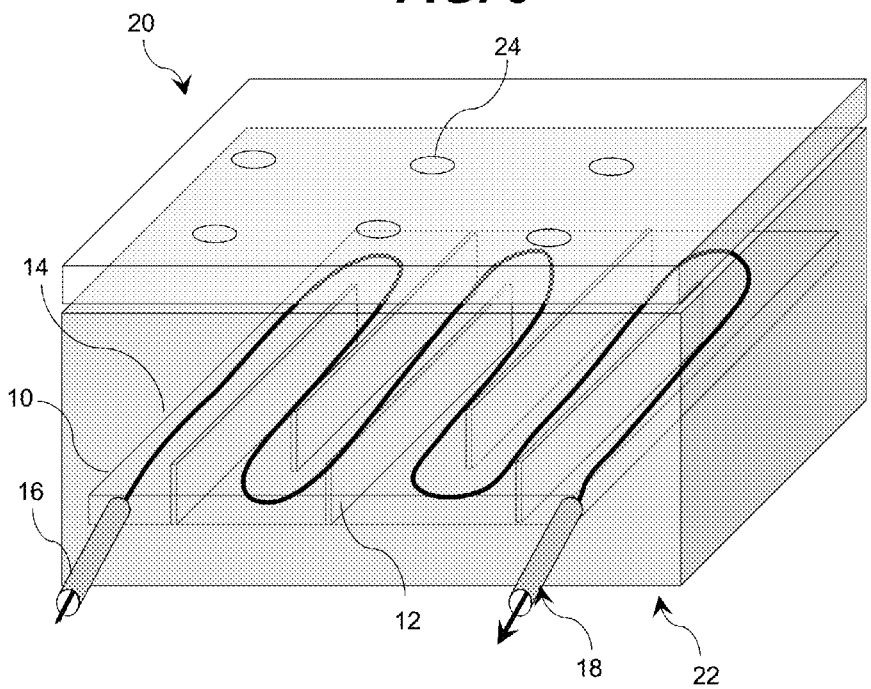
FIG. 3 shows an illustrative disinfection system including an ultraviolet transparent enclosure according to an embodiment of the invention.

The UV transparent enclosure 10 can be utilized with a disinfection system. Turning now to FIG. 3, an illustrative disinfection system 20 according to an embodiment is shown. The disinfection system 20 includes the UV transparent enclosure 10 with the welded separators 12 to create the channel 14 for media to flow through from the inlet 16 to the outlet 18. The UV transparent enclosure 10 is located within an outer enclosure 22 that can be configured to confine and recycle the UV radiation generated by a set of ultraviolet radiation sources 24. The set of ultraviolet radiation sources 24 can comprise any combination of one or more ultraviolet radiation emitters. For example, the set of ultraviolet radiation sources 24 can include a high intensity ultraviolet lamp (e.g., a high intensity mercury lamp), a discharge lamp, an ultraviolet light emitting diode (LED), super luminescent LEDs, laser diodes, and/or the like. In an embodiment, the set of ultraviolet radiation sources 24 includes a set of light emitting diodes manufactured with one or more layers of materials selected from the group-III nitride material system (e.g., $Al_xIn_yGa_{1-X-Y}N$, where $0 \leq x, y \leq 1$, and $x+y \leq 1$ and/or alloys thereof).

When an embodiment of the set of ultraviolet radiation sources 24 described herein includes multiple ultraviolet radiation sources 24, it is understood that the ultraviolet radiation sources 24 can all be configured to emit radiation of substantially the same wavelength or of multiple distinct wavelengths. To this extent, an embodiment of a set of ultraviolet radiation sources 24 described herein can include multiple distinct ultraviolet radiation sources having multiple distinct peak emission wavelengths, where the peak emission wavelengths are separated by at least a full width at half maximum. Additionally, the set of ultraviolet radiation sources 24 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, towards the media flowing through the channel 14. Illustrative wave guiding structures include, but are not limited to, a plurality of ultraviolet fibers, each of which terminates at an opening, a diffuser, and/or the like.

Figure 2B:
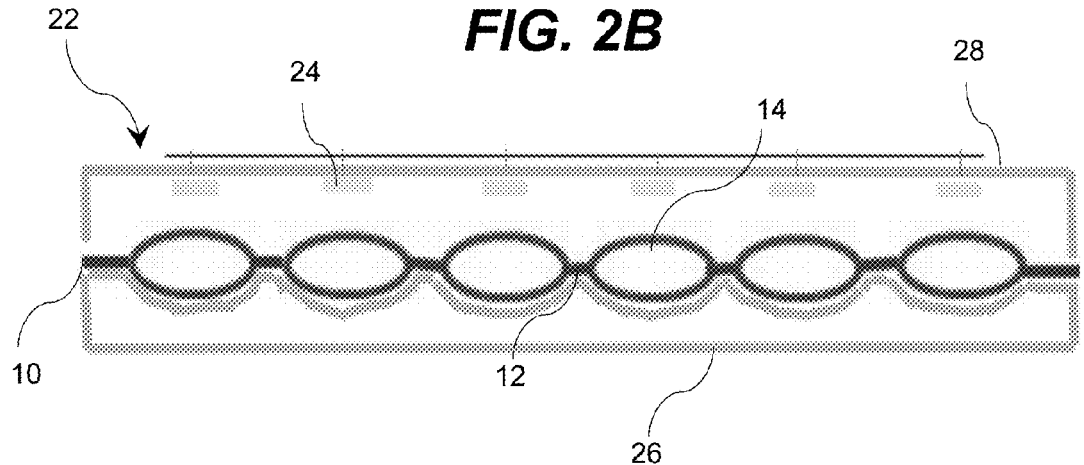

The internal surfaces of the outer enclosure 22 can include a material that is highly reflective to UV radiation in order to recycle the UV radiation within the outer enclosure 22, such as GORE® Diffuse Reflector Product (DRP®) film, polytetrafluoroethylene (PTFE), Spectralon polymers, Valar UV material, and/or the like. In an embodiment, the internal surfaces of the outer enclosure 22 can be diffusively reflective to UV radiation and chemically stable to UV radiation. Turning now to FIG. 2B, a cross sectional view of a disinfection system according to an embodiment is shown. The UV transparent enclosure 10, as shown in FIG. 2A, is located within the outer enclosure 22. In this embodiment, the outer enclosure 22 can include a bottom portion 26 that holds the UV transparent enclosure 10. The bottom portion 26 can be made from stamped aluminum that is reflective to the UV radiation or be a three-dimensional (3D) printed polymer that is covered with a reflective film (e.g., GORE® DRP® film, PTFE, Spectralon polymers, and/or the like). The UV transparent enclosure 10 can be covered by a top portion 28 that is also reflective to the UV radiation. The top portion 28 can include a printed circuit board (PCB) for the set of ultraviolet radiation sources 24, and any drivers, ultraviolet transmitters (UVT), flow indicators, flow valves, sensors (e.g., for sensing a transparency of the media to be disinfected), devices for mixing the media to be disinfected, filters (e.g., for filtering contaminants from the media prior to determining the transparency of the media), and/or the like.

Turning back to FIG. 3, by having the UV transparent enclosure 10 within the outer enclosure 22, the set of ultraviolet radiation sources 24 can be separated from the media to be disinfected within the channel 14, which can extend the life of the set of ultraviolet radiation sources 24. Further, the UV transparent enclosure 10 can be easily replaceable. The outer enclosure 22 can help to recycle the UV radiation generated by the UV radiation sources 14, so that the efficiency of the disinfection is improved.

Figure 4:
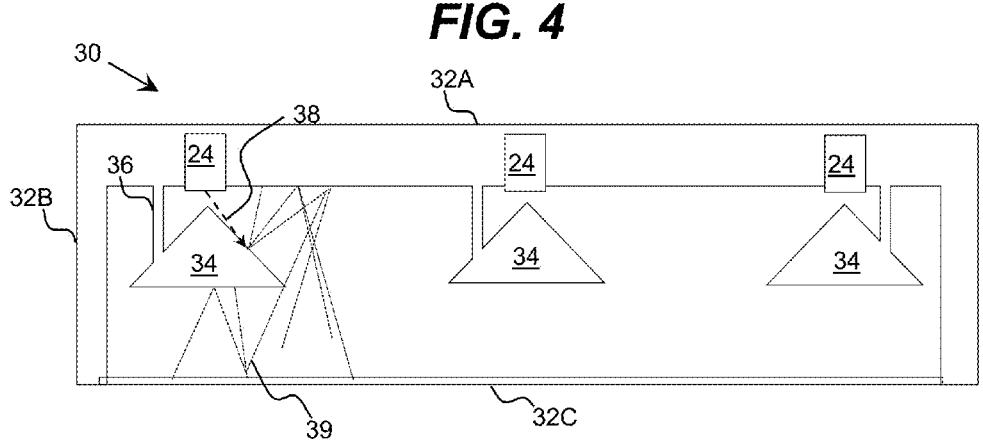
FIG. 4 shows an assembly of UV radiation sources for diffusively emitting UV radiation according to an embodiment of the invention.

The set of ultraviolet radiation sources 24 can be integrated as part of the outer enclosure 22 or be in a separate component separable from the outer enclosure 22, which is configured to provide UV radiation. In an embodiment, the set of ultraviolet radiation sources 24 can be part of an UV diffusive illuminator that is located adjacent to the outer enclosure 22, as shown in FIG. 3. Turning now to FIG. 4, an illustrative assembly of the set of ultraviolet radiation sources 24 in an UV diffusive illuminator 30 according to an embodiment is shown. The illuminator 30 can include a plurality of surfaces 32A-C. A first surface 32A and a second surface 32B can be highly reflective to UV radiation. The third surface 32C can include a partially transparent film for allowing at least a portion of the UV radiation to pass through. The partially transparent film can include a material such as fluorinated ethylene propylene (FEP), fluorinated ethylene propylene co-polymer (EFEP), Perfluoroalkoxy (PFA), tetrafluoroethylene hexafluoropropylene vinylidene fluoride (THV), and/or the like. In an embodiment, the set of ultraviolet radiation sources 24 can be attached to the first surface 32A. The illuminator 30 can include a set of reflecting mirrors 34, each of which is located directly beneath an ultraviolet radiation source 24. The reflecting mirrors 34 can comprise a highly diffusive ultraviolet radiation material, such as a highly ultraviolet reflective expanded polytetrafluoroethylene (ePTFE) membrane (e.g., GORE® Diffuse Reflector Product (DRP)), and/or the like. In an embodiment, the reflecting mirrors 34 can comprise a fluoropolymer, such as fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), Teflon, and/or the like. In still another embodiment, the reflecting mirrors 34 can be partially UV reflecting, partially UV transparent. For example, the reflecting mirrors 34 can comprise an UV reflective film over an UV transparent film. In an embodiment, the reflecting mirrors 34 can be configured to provide specular reflection and can comprise, for example, polished aluminum, and/or the like.

The reflecting mirrors 34 are attached via legs 36 to the first surface 32A of the illuminator 30. In operation, an original incident of ultraviolet radiation 38 from the ultraviolet radiation source 24 can be diffusively reflected by the reflecting mirror 34 and then again diffusively reflected by the surfaces (e.g., first surface 32A). This diffusive UV radiation 39 exits the illuminator 30 through the partially transparent, partially reflective surface (e.g., third surface 32C).

The reflecting mirrors 34 and the high diffusive reflectivity of the surfaces 32A-B of the illuminator 30 distribute and diffusively reflect the ultraviolet radiation from the ultraviolet radiation sources 24 such that the third surface 32C of the illuminator 30 has an approximately Lambertian reflectance.

It is understood that the ultraviolet radiation sources can be positioned anywhere within the illuminator, including attached to a surface of the cavity of the illuminator (e.g., illuminator 30 in FIG. 4) or in the interior of the cavity. To this extent, turning now to FIGS. 5A and 5B, an illustrative illuminator 40 according to an embodiment is shown. In this case, the ultraviolet radiation sources 24 are positioned within the interior of illuminator 40 and are configured to direct ultraviolet radiation towards the first surface 32A. In an embodiment, at least 90% of the ultraviolet radiation is directed towards the first surface 32A of the illuminator 40. The ultraviolet radiation sources 24 can be mounted on a mounting mesh 42 using any solution. Since at least the first surface 32A of the illuminator 40 is at least 70% reflective, the ultraviolet radiation generated by the ultraviolet radiation sources 24 is diffusively reflected off of the first surface 32A and scattered throughout the illuminator 40. The mounting mesh 42 can include a plurality of voids 44 to allow the diffused ultraviolet radiation to transmit past the mounting mesh 42 towards the third surface 32C to exit the illuminator 40. The mounting mesh 42 can also include a material that is highly reflective, such as a highly ultraviolet reflective expanded polytetrafluoroethylene (ePTFE) membrane (e.g., GORE® Diffuse Reflector Product), and/or the like, to improve the overall light intensity distribution and facilitate light scattering and recirculation throughout the illuminator 40.

Figure 6:
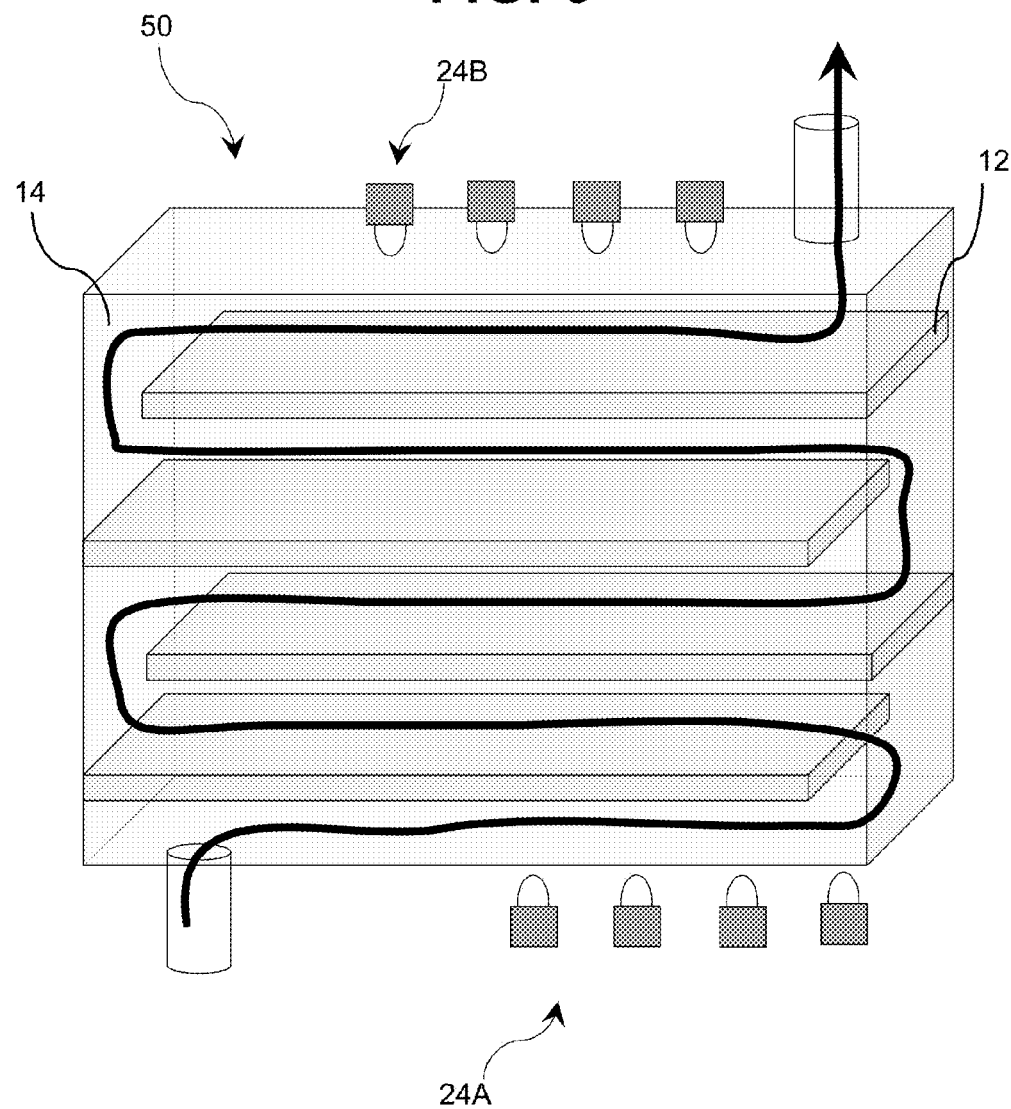
FIG. 6 shows an illustrative disinfection system according to an embodiment of the invention.

Turning now to FIG. 6, an illustrative UV transparent enclosure 50 according to an embodiment is shown. The UV transparent enclosure 50 includes a channel 14 that is created by a plurality of welded separators 12. In this embodiment, the plurality of welded separators 12 can include a material that is transparent to UV radiation. Therefore, the UV radiation generated by the set of ultraviolet radiation sources 24 can penetrate all portions of the channel 14, even though there is only a first set of ultraviolet radiation sources 24A located at the beginning of the channel 14 and a second set of ultraviolet radiation sources 24B located at the end of the channel 14. This configuration of ultraviolet radiation sources 24A, 24B allows for maximum exposure of the media within the channel 14 to the UV radiation. In an embodiment, the thickness of the channel 14 can be selected to allow disinfection of an opaque fluid flowing there through. For example, the UV transparent enclosure 50 can be designed for a fluid with the absorption coefficient of milk. Consider a fluid with the absorption coefficient a. Then, the transmission is given by $I=I_0 \exp(-ax)$, or $$-\ln\left(\frac{I}{I_0}\right)/a = x,$$

wherein I is the transmitted intensity, $I_0$ is the emitted intensity, and x is the path length of the ultraviolet radiation through the material, which corresponds to the material thickness. For $$c = \frac{I}{I_0}$$

being in the range of 0.2-0.5, there is still sufficient disinfection action at the distances x:

$$-\ln\left(\frac{I}{I_0}\right)/a = x.$$

Thus, this thickness can be utilized as a characteristic thickness of the channel 14 in the proximity of an UV radiation source 24 to ensure adequate dose to the opaque fluid at the appropriate flow rates.

Figure 7:
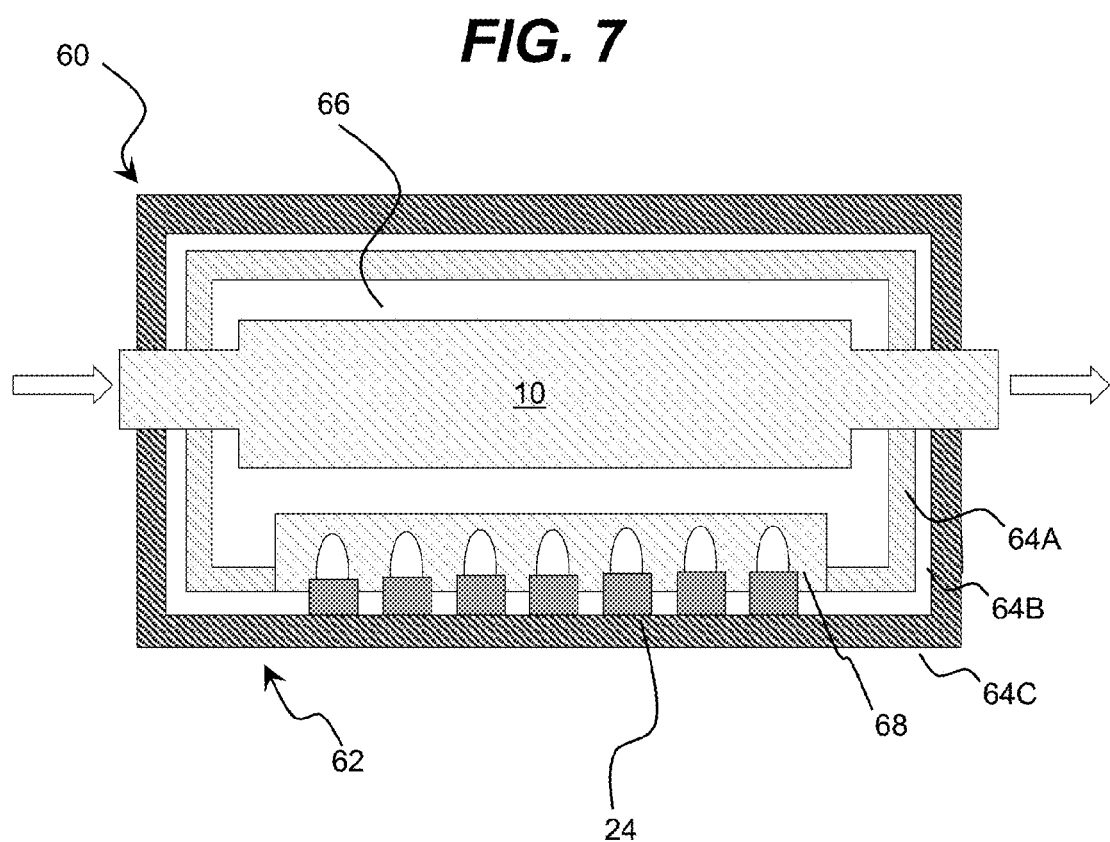
FIG. 7 shows an illustrative disinfection system according to an embodiment of the invention.

Turning now to FIG. 7, an illustrative disinfection system 60 according to an embodiment of the invention is shown. In this embodiment, the UV transparent enclosure 10 is the channel through which the media to be disinfected flows through. Although the plurality of welded structures 12 shown in other embodiments (e.g., FIG. 1B, 2A, 2B, 3) are not shown in this UV transparent enclosure 10, it is understood that the plurality of welded structures 12 can be included. The UV transparent enclosure 10 is located within an outer enclosure 62 which includes a plurality of layers 64A-C. A first innermost layer 64A of the outer enclosure 62 can include a polymer material that is transparent to UV radiation, such as FEP, EFEP, THV, and/or the like. A second layer 64B of the outer enclosure 62 can be a gap that can be filled with, for example, air. A third layer 64C of the outer enclosure 62 can include a reflective material that is reflective to UV radiation, such as PTFE, Teflon, GORE® DRP®, Spectralon, Valar UV material, and/or the like. In an embodiment, a region 66 between the UV transparent enclosure 10 and the outer enclosure 62 can be filled with a distilled highly transparent fluid that has an index of refraction that is similar to the index of refraction of the first layer 64A. In an embodiment, the index of refraction of the highly transparent fluid is within 20% of the index of refraction of the first layer 64A. The outer enclosure 62 can also include a UV transparent cover 68 to physically isolate the set of UV radiation sources 24. In general, the UV transparent cover 68 can comprise a fluoropolymer that can encapsulate the set of UV radiation sources 24. Although the UV transparent cover 68 is located on one side of the outer enclosure 62, it is understood that this is for illustrative purposes only and that the UV transparent cover 68 can be located on any side of the outer enclosure 62. Furthermore, although not shown, the UV transparent cover 68 can include an illuminator, such as the illuminators 30, 40 shown in FIGS. 4 and 5A-B. Any other metal, electrical, optical, and/or the like components that are required for the functionality of the disinfection system 60 can be located in the UV transparent cover 68 or a separate compartment that is not shown, so that they do not directly interact with the fluid in region 66 or the media to be disinfected within the UV transparent enclosure 10. Additionally, the UV radiation is capable of total internal reflection (TIR) at the interface of the first layer 64A and the second layer 64B due to the reduction in the index of refraction for the UV radiation traveling at angles above a critical angle. The layers 64A-C of the outer enclosure 62 provide an omnidirectional mirror to reflect TIR rays and has a high reflectivity for rays at angles close to the critical angle. Also, the reflection from the third layer 64C provides a highly diffusive reflectance for surface normal incident rays.

Figure 8A:
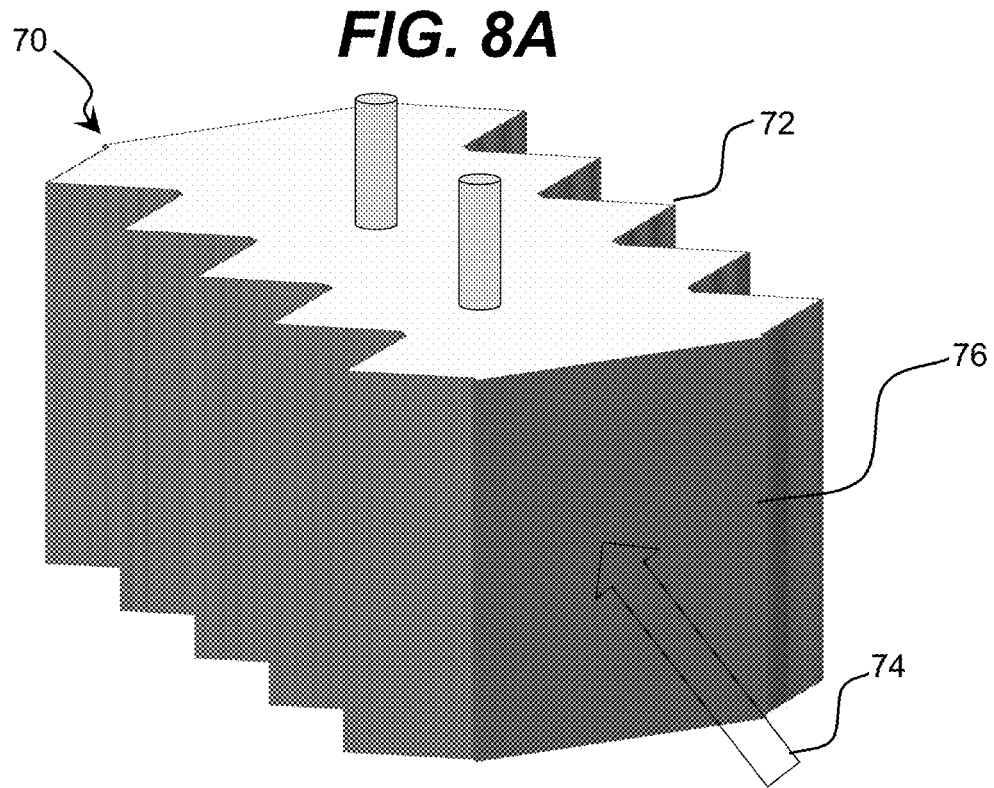
FIGS. 8A and 8B show an illustrative ultraviolet transparent enclosure according to an embodiment of the invention.
Figure 8B:
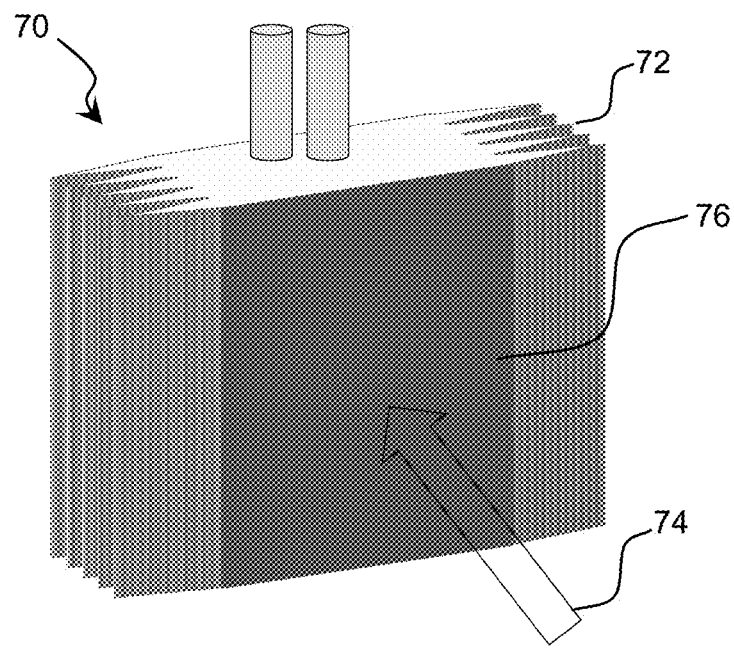

In an embodiment, the volume of any of the embodiments of the UV transparent enclosure can be the lateral area multiplied by the height of the enclosure, and the height of the enclosure can be adjustable. Turning now to FIGS. 8A and 8B, an illustrative ultraviolet transparent enclosure 70 according to an embodiment of the invention is shown. In this embodiment, the exterior surfaces of the ultraviolet transparent enclosure 70 can include corrugated edges 72. The UV radiation can be applied at any side of the ultraviolet transparent enclosure 70. For example, the UV radiation 74 can be applied to a first side 76. The corrugated edges 72 of the ultraviolet transparent enclosure 70 are provided so that the physical effective thickness of the ultraviolet transparent enclosure 70 can be changed, as shown in FIGS. 8A and 8B, where the enclosure volume is modified. The thickness of the ultraviolet transparent enclosure 70 can be adjusted based on the transparency of the media to be disinfected, as shown by the formula $$-\ln\left(\frac{I}{I_0}\right)/a = x.$$

It is understood that not all surfaces of the enclosure 70 need to be transparent to UV radiation. It is also understood that this enclosure 70 can be incorporated into any disinfection system provided herein.

Figure 9A:
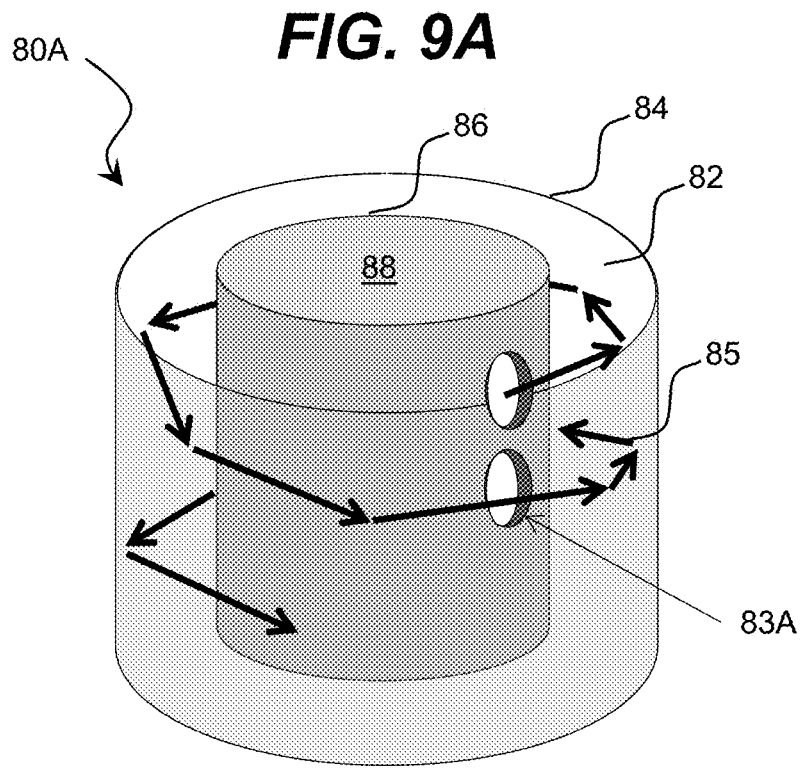
FIGS. 9A and 9B show illustrative UV transparent enclosures according to embodiments of the invention.
Figure 9B:
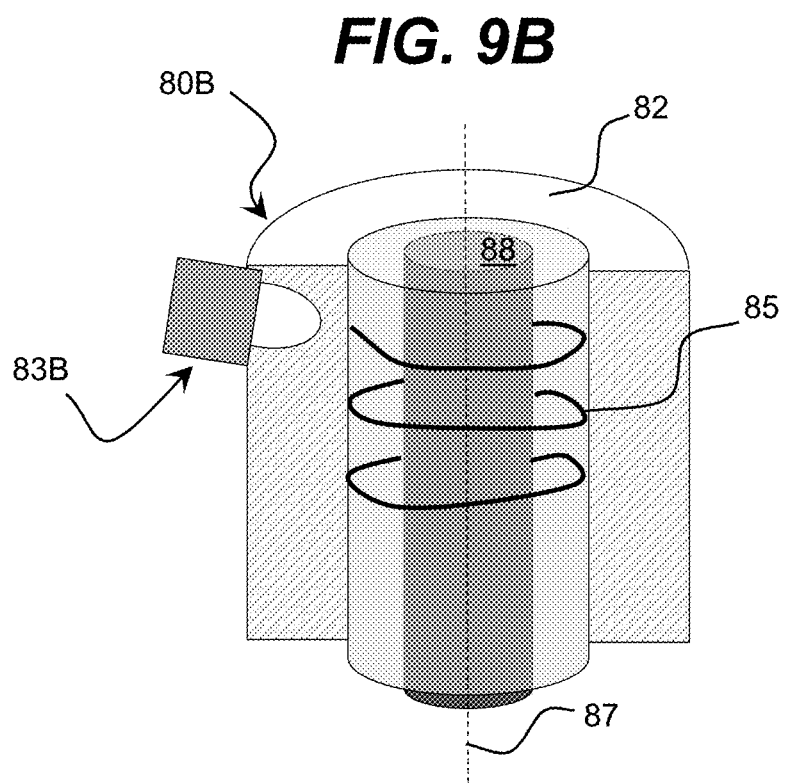

Turning now to FIGS. 9A and 9B, illustrative UV transparent enclosures according to embodiments are shown. The UV transparent enclosures 80A, 80B shown in FIGS. 9A and 9B can be utilized for the disinfection of media that is relatively transparent to UV radiation. For example, the transmission of the disinfection media is higher than approximately 1 centimeter. For this media, the recycling of the UV radiation can be provided through the TIR of the UV radiation at the interface of the media and the UV transparent enclosure. To obtain the TIR of the UV radiation, a degree of collimation of the UV radiation is required. A parabolic reflector can be part of the illuminator 83A or 83B. For example, the illuminator 83A or 83B can comprise a single or array of UV LED sources placed in a focal point of the parabolic reflector. In all embodiments, whether the use of parabolic reflector, or a set of any other optical elements (such as lenses) is used, the UV radiation from the illuminator 83A or 83B is collimated. It is understood that absolute collimation is not necessary, and it is sufficient if at least 50% of the emitting radiation has a collimated component of radiation within solid angle of about 0.1 which corresponds to cone angle of about 10 degrees. The UV transparent enclosure 80A shown in FIG. 9A includes a cylindrical ring 82. The cylindrical ring 82 includes an exterior UV transparent surface 84 and an interior UV transparent surface 86. The media to be disinfected is within the cylindrical ring 82, between surfaces 84, 86. Both the exterior and interior UV transparent surfaces 84, 86 can include a polymer that is transparent to UV radiation. A cylinder 88 can be located within the cylindrical ring 82 and adjacent to the interior UV transparent surface 86. In an embodiment, a layer of water can be located between the cylinder 88 and the cylindrical ring 82. For typical UV transparent materials that can be used to enclose water, the index of refraction either match the index of refraction of enclosed water or is higher. For example, the fluoropolymers are readily available and can be used to manufacture UV transparent enclosing ring having exterior and interior UV transparent surfaces 84 and 86 respectively. The fluoropolymers have refractive index similar to that of water (e.g., approximately 1.3). In another embodiment, the transparent enclosing ring can be made of fused silica or sapphire having refractive index larger than that of enclosed liquid. In this embodiment, the cylinder 88 can comprise a reflective or transparent material and house the set of ultraviolet radiation sources, which provide collimated UV radiation. In FIG. 9A, the illuminator 83A is placed within the cylinder 88 and UV radiation 85 is emitted into the cylindrical ring 82 of the UV transparent enclosure 80A. In FIG. 9B, the illuminator 83B is placed within the cylindrical ring 82 of the UV transparent enclosure 80B and UV radiation 85 is directed to be between the cylindrical ring 82 and the cylinder 88.

Figure 10A:
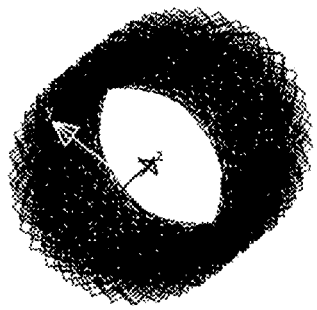
FIGS. 10A-10D show ray tracing simulations for the illustrative disinfection system shown in FIGS. 9A and 9B according to an embodiment.
Figure 10B:
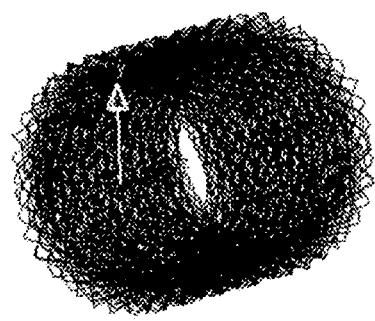
Figure 10C:
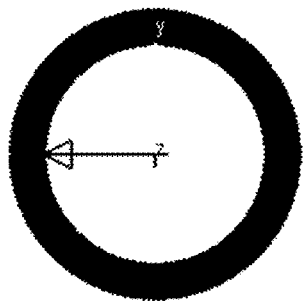
Figure 10D:
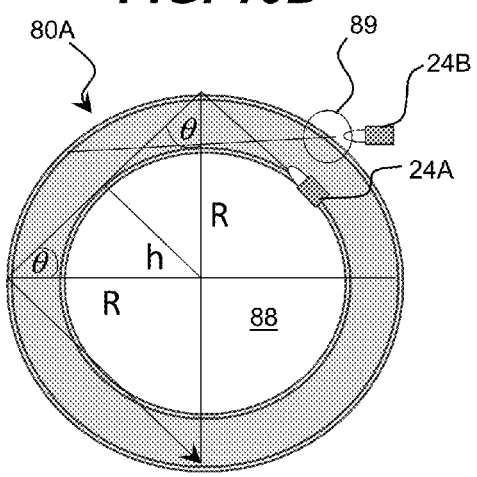

FIGS. 10A-10C show the ray tracing simulations for the UV transparent enclosure 80A shown in FIG. 9A, in which the ultraviolet radiation sources are located tangential to the inside of the cylinder 88. The UV radiation rays exiting the source impinge the boundary of the interior UV transparent surface 86 and air at or above the critical angle, which results in TIR. The rays then propagate in a circular fashion, as shown in FIGS. 10A-10C, which results in a concentration of intensity in the cylindrical ring 82. As shown in FIG. 10D, a radius of the cylinder 88, h, can be selected based on an index of refraction of the media to be disinfected. For example, the radius h can be defined by $h=R*\sin(\theta)=R*(n_2/n_1)$, where R is the radius of the UV transparent enclosure 80, $n_2$ is the index of refraction of the ambient (e.g., $n_2=1$ for air), $n_1$ is the index of refraction of the media to be disinfected, and $\theta$ is defined by the angle of reflection shown in FIG. 10D for the ultraviolet radiation source 24A. In another embodiment, $n_1$ can be the index of refraction of the material of the UV transparent enclosure 80A. In an embodiment, the radius of the cylinder 88, h, is approximately 5% smaller than a value obtained by calculating the product of the outer radius, R, times the ratio of index of refractions of the outside media, $n_2$, and index of refraction, $n_1$, of the smallest of: the UV transparent material comprising the cylinder 88 or the media requiring disinfection evaluated for the wavelength of the emitted radiation.

Figure 11A:
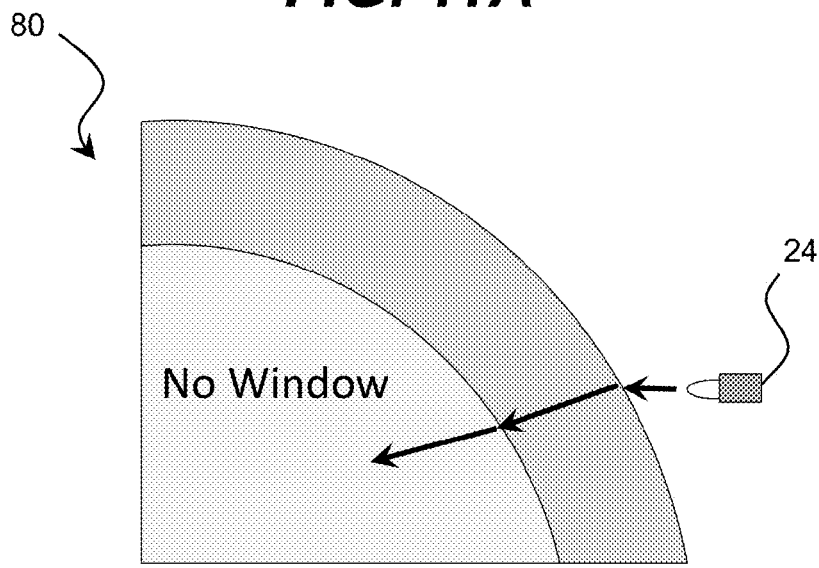
FIGS. 11A and 11B show partial cross sectional views of an illustrative ultraviolet transparent enclosure without a window and with a window, respectively, according to embodiments of the invention.
Figure 11B:
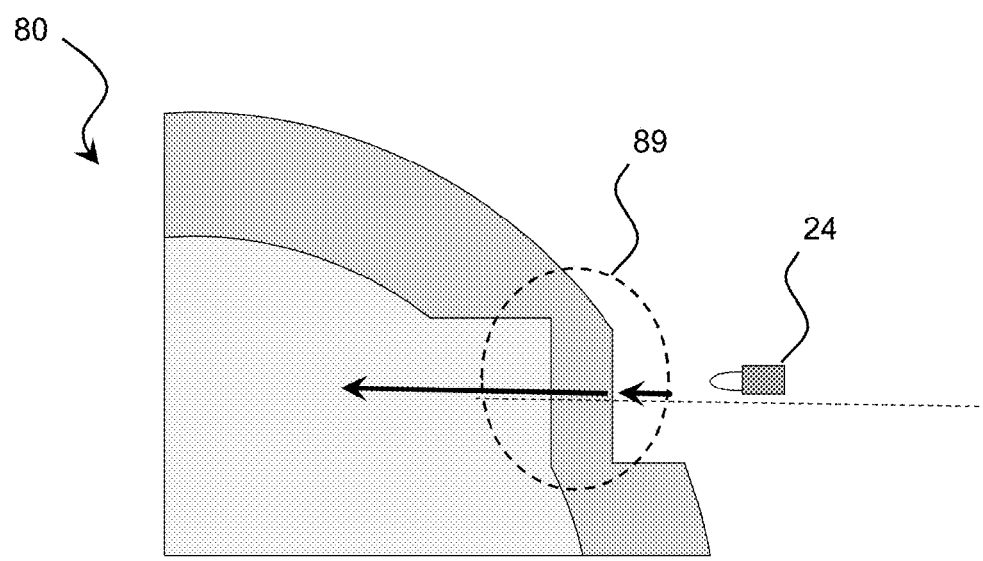

An ultraviolet radiation source 24B can be located within the cylindrical ring 82 and the UV radiation can be provided through a window 89. In an embodiment, the window 89 can be designed to not alter the direction of the UV radiation. In an embodiment, the material for the window 89 can be formed of the same material as the cylinder 88, fused silica, sapphire, and/or the like. For example, FIGS. 11A and 11B illustrate a portion of the ultraviolet transparent enclosure 80 without a window and with a window, respectively, according to embodiments of the invention. In FIG. 11A, when there is no window present, the direction of the UV radiation changes as it goes through the UV transparent enclosure 80 and into the channel 14 where the media to be disinfected is located. In FIG. 11B, the UV radiation goes through the window 89 of the UV transparent enclosure 80. In the embodiment shown in FIG. 11B, the UV radiation forms a helical ray path. In an alternative embodiment, no window is utilized and the ultraviolet radiation source 24 is angled appropriately to account for the change in direction of the UV radiation.

Figure 12A:
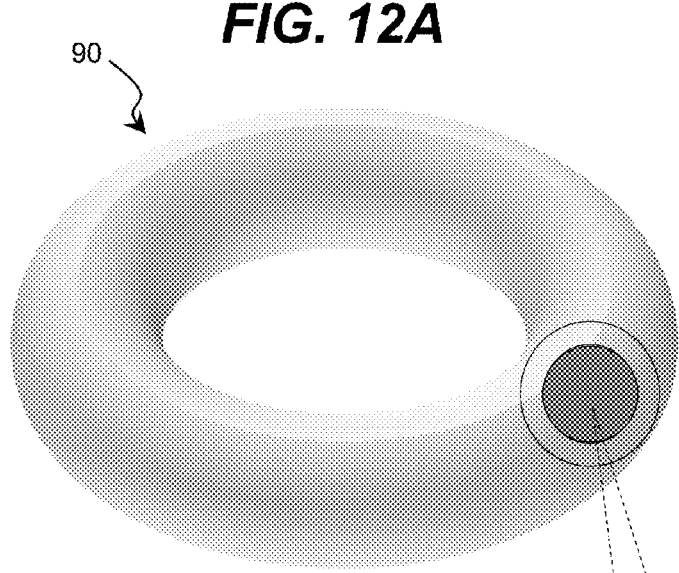
FIG. 12A shows a toroid shaped enclosure according to an embodiment of the invention and 12B shows a cross sectional view of the toroid shaped enclosure according to an embodiment of the invention.
Figure 12B:
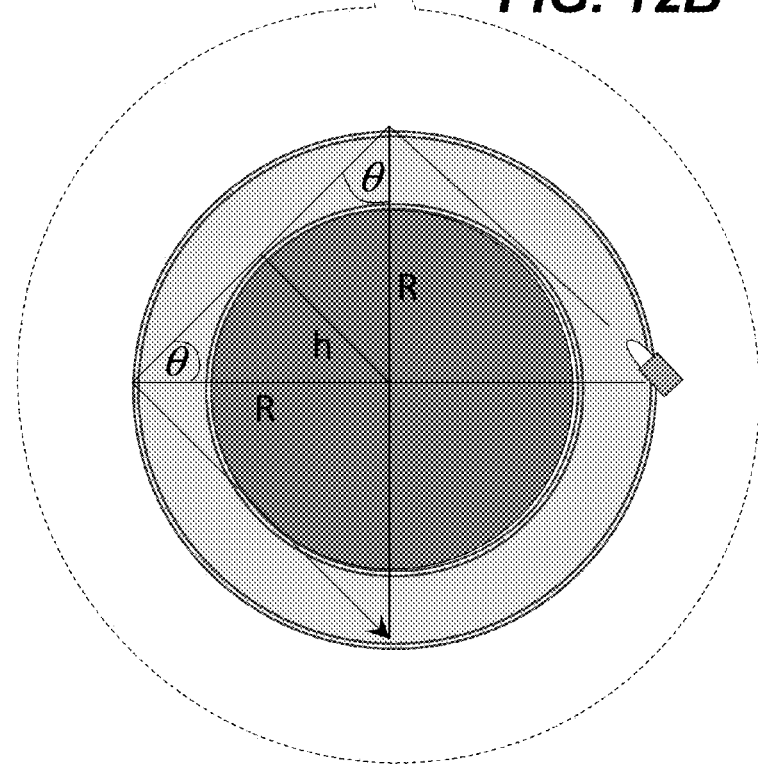

Turning now to FIGS. 12A and 12B, an illustrative UV transparent enclosure 90 according to an embodiment is shown. In this embodiment, the UV transparent enclosure 90 is a toroid shape, which can, for example, promote TIR. The toroid shape of the UV transparent enclosure 90 can ensure that loss of UV radiation is primarily through absorption within the media to be disinfected, within the walls of the enclosure 90, and associated with the eventual loss of collimation of UV radiation and its escape from the enclosure 90. In order to reduce the effect of loss of collimation, the initial direction of UV radiation can be selected to be at an angle higher than the critical angle needed for total internal reflection, as shown in FIG. 12B. The embodiment of the UV transparent enclosure 90 shown in FIGS. 12A and 12B incorporates all the features of other embodiments shown herein, including FIGS. 9A-11B, along with the center axis 87 of the cylinder 88 in FIG. 9B including a curvature that results in toroidal shape.

It should be understood that the embodiments shown in FIGS. 9A-12B only illustrate the utilization of total internal reflection of collimated UV radiation to improve recycling of UV radiation. Other embodiments that utilize such reflection are possible including differently shaped disinfection enclosures and UV radiation sources that are oriented to provide such total internal reflection. It is further understood that the embodiments of the UV transparent enclosure discussed herein do not have to comprise a UV transparent polymer along all surfaces and can include reflective regions as well. More specifically, the UV transparent enclosure may also include holes or regions having no UV transparent enclosure at all. For example, the liquid requiring disinfection may comprise a laminar water stream coming out of a nozzle (such as tap), which can freely fall due to the action of gravity. The nozzle can be equipped with a portion of UV transparent enclosure as shown in FIGS. 9A-12B that contains UV radiation sources. In addition, the flow of the media to be disinfected can have a cylindrical pillar element located in the middle of the flow, similar to the cylinder 88 shown in FIG. 9A. The cylinder 88 can improve the laminar characteristics of the flow of the media to be disinfect and can be made of UV reflective material. The UV radiation sources can create a light which can be waveguided along the flow of the media to be disinfected, circling around the media as shown in the ray tracing simulations of FIGS. 10A-10C.

In any of the embodiment of the ultraviolet transparent enclosure provided herein, a catalyst can be introduced to the media to enhance the disinfection of the media. Furthermore, in all embodiments of the ultraviolet transparent enclosure, the inlet and outlet can be connected to repeat the disinfection cycle for a designated number of times to ensure proper disinfection. The number of times can be dependent upon a level of disinfection that is required.

Figure 13:
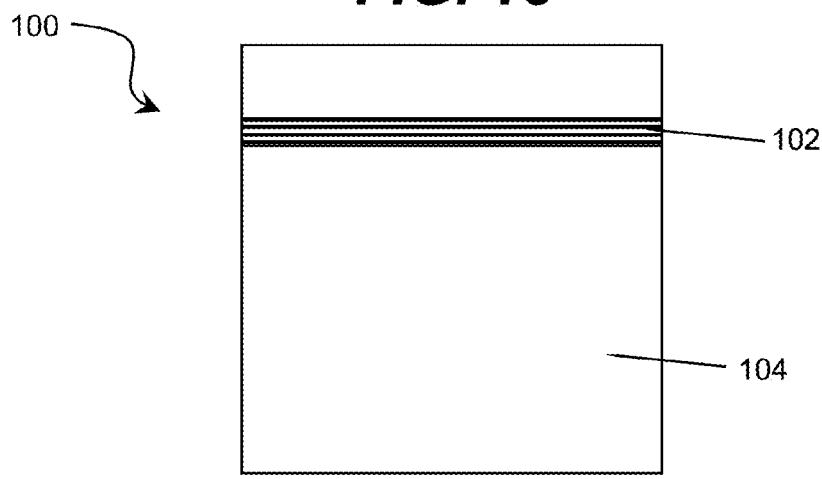
FIG. 13 shows an ultraviolet transparent enclosure in the form of a resealable enclosure having a zipper mechanism according to an embodiment.

FIG. 13 shows an ultraviolet transparent enclosure 100 in the form of a resealable enclosure having a zipper mechanism 102 on a resealable side surface 104 according to an embodiment. The ultraviolet transparent enclosure 100 can include any of the aforementioned UV transparent polymers that have anti-biofouling properties. The zipper mechanism 102 on the resealable side surface 104 provides access to an interior portion of the ultraviolet transparent enclosure 100. In particular, opening the zipper mechanism 102 permits access to the interior portion of the ultraviolet transparent enclosure 100, while closing the zipper mechanism 102 seals off the interior portion, restricting entry and exit from the enclosure 100. In one embodiment, the zipper mechanism 102 can include an interlocking groove and ridge assembly formed on the resealable side surface 104 of the ultraviolet transparent enclosure 100. In one embodiment, the interlocking groove and ridge assembly can be formed across the width of the resealable side surface 104. In this manner, the interlocking groove and ridge can be engaged and disengaged to seal or unseal the interior portion of the ultraviolet transparent enclosure 100. It is understood that the interlocking groove and ridge assembly does not necessarily have to extend across the whole width of the resealable side surface 104. The length of the interlocking groove and ridge assembly across the width of the resealable side surface 104 can depend on the size of the ultraviolet transparent enclosure 100, the size of the interior portion of the ultraviolet transparent enclosure 100, and on how much access to the interior portion of the enclosure 100 is desired. Furthermore, it is understood that the interlocking groove and ridge assembly can be placed across the height of the enclosure 100 or even oriented to extend in other configurations such as for example, diagonally from one corner of the enclosure to another corner.

Although other embodiments described herein are directed to using ultraviolet transparent enclosures for the disinfection of a flow of media, the ultraviolet transparent enclosure 100 is suitable for other applications. For example, the ultraviolet transparent enclosure 100 can be used for the disinfection of articles placed within the enclosure. Alternatively, the enclosure can disinfect articles while physically separating them from UV radiation. In these examples, it may be desirable to have the ultraviolet transparent enclosure 100 formed with one of the aforementioned ultraviolet transparent polymers and have a transparency to at least 30% of radiation directed at the normal incidence to the surface of the ultraviolet transparent enclosure 100.

Figure 14:
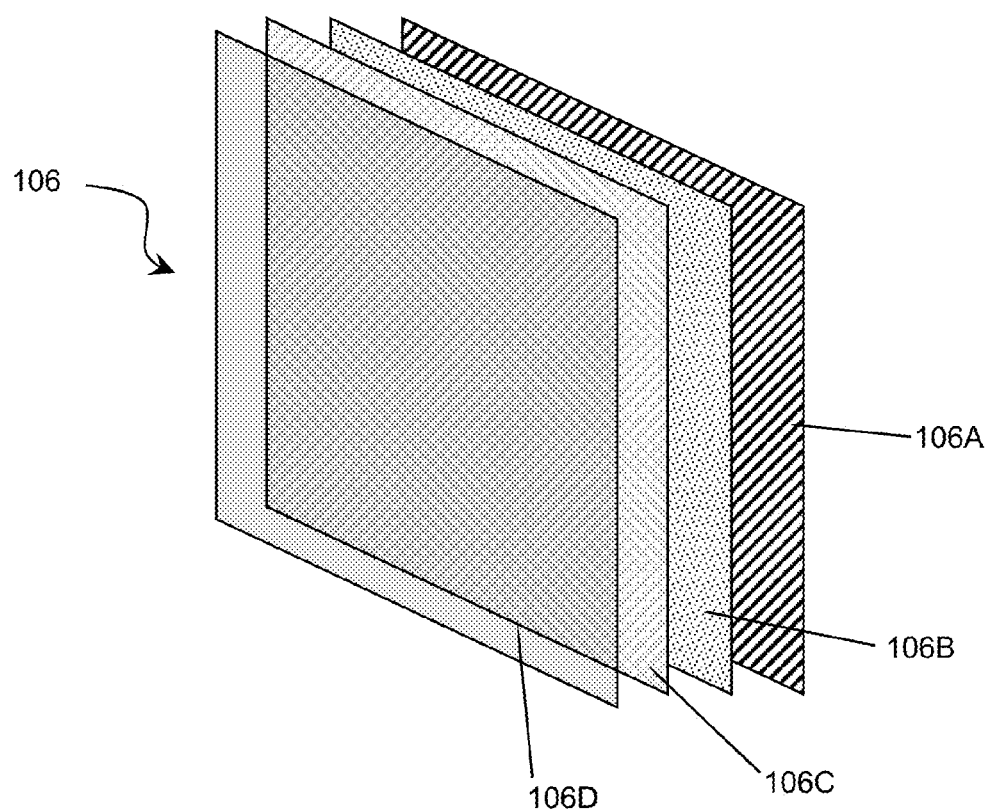
FIG. 14 shows a schematic of ultraviolet transparent sub-layers that can form an ultraviolet transparent enclosure according to an embodiment.

FIG. 14 shows a schematic of ultraviolet transparent sub-layers that can be used to form an ultraviolet transparent enclosure according to an embodiment. In one embodiment, the ultraviolet transparent sub-layers can take the form of a laminate 106 of sub-layers that have anti-biofouling properties and are transparent to at least a predetermined amount of radiation directed at the normal incidence to a surface. The ultraviolet transparent laminate 106 of sub-layers of FIG. 14 is shown with sub-layers 106A, 106B, 106C and 106D. Sub-layer 106D which can be the outer layer of the ultraviolet transparent enclosure, e.g., the layer furthest away from the object undergoing disinfection can have durable and protective features. For example, the sub-layer 106D can include an ultraviolet transparent polymer that has a high resistance to tearing or puncturing. In addition, the sub-layer 106D can have anti-biofouling properties. A fluoropolymer layer is an example of an ultraviolet transparent polymer that can have a high resistance to tearing or puncturing, and have anti-biofouling properties. A non-exhaustive list of fluoropolymers that are suitable for the sub-layer 106D can include a thin layer of Teflon® or a layer of ethylene tetrafluoroethylene (ETFE) or a similar fluoropolymer.

Sub-layer 106C, the next ultraviolet transparent layer in from the sub-layer 106D, can include a layer of diffusive properties for the purpose of controlling the intensity of the UV radiation over the area. For example, the sub-layer 106C with diffusive properties can redistribute UV radiation to have more uniform coverage over an article or matter being irradiated. A fluoropolymer layer with embedded diffusive domains is an example of an ultraviolet transparent polymer that can be used as sub-layer 106C. A non-exhaustive list of fluoropolymers with embedded diffusive domains can include $SiO_2$ domains and $Al_2O_3$ domains. In another embodiment, a fluoropolymer layer with embedded grains, fibers or fragments can be used to form the sub-layer 106C with diffusive properties. For example, the sub-layer 106C can have powders of ultraviolet transparent material or fragments of different fluoropolymers.

In one embodiment, the sub-layer 106C can have structures or features formed therein that can improve light scattering with an ultraviolet transparent enclosure in which the laminate of sub-layers 106A, 106B, 106C and 106D can be used. For example, the sub-layer 106C can have, but is not limited to a light guiding structure (e.g., a waveguide, a plurality of ultraviolet fibers), a groove structure, air cavities and components for directing and/or delivering emitted radiation to a particular location/area, in a particular direction, in a particular pattern, and/or the like.

Sub-layer 106B, the next ultraviolet transparent layer in from the outer surface, can have fluorescent properties. In one embodiment, an ultraviolet transparent layer with fluorescent properties can be beneficial in that it can aid in showing the distribution of ultraviolet radiation over a surface of the ultraviolet transparent enclosure in which the laminate of sub-layers 106A, 106B, 106C and 106D can be used. In addition, an ultraviolet transparent layer with fluorescent properties can serve as an indicator of the presence of ultraviolet radiation within the enclosure. A fluoropolymer layer with ultraviolet fluorescence is an example of an ultraviolet transparent polymer that can be used as sub-layer 106B. A non-exhaustive list of fluoropolymers with ultraviolet fluorescence can include fluorinated ethylene propylene (FEP), fluorinated ethylene propylene co-polymer (EFEP), Perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), Teflon, and/or the like.

Sub-layer 106A, which can be the last layer of the ultraviolet transparent enclosure that is adjacent to the article, substance, or extremity that is to undergo disinfection, can include an ultraviolet transparent film with anti-biofouling properties. For example, sub-layer 106A can include a thin layer of Teflon®. In another embodiment, the sub-layer 106A can further contain a thin layer or a set of regions that comprise a photo-catalyst activated by ultraviolet radiation for disinfection. An example of a photo-catalyst can include $TiO_2$, however, it is understood that other photo-catalysts known in the art can be used.

The laminate 106 structure of sub-layers 106A, 106B, 106C and 106D depicted in FIG. 14 can be partially transparent to ultraviolet radiation. In one embodiment, the laminate 106 structure of sub-layers 106A, 106B, 106C and 106D can be transparent to at least 30% of the radiation directed at the normal incidence to the surface.

Furthermore, the laminate 106 can have a reflective film that reflects at least 30% percent of radiation having a target wavelength, which is radiated at a normal incidence to an interface of the laminate. The reflective film can have reflective properties that are over a fraction of a surface area of a sublayer. In one embodiment, the reflective film can include an aluminum film. In another embodiment, the reflective film can include a diffusively reflective material such as PTFE. In one embodiment, the reflective film can be part of the laminate structure 106 of sublayers 106A-106D. For example, the reflective film can take the form of a layer that is separate from the sub-layers 106A-106D. In one embodiment, the reflective film can be an embedded sub-layer that is protected from the ambient and from the article, substance, or extremity that is to undergo disinfection.

It is understood that the number of sub-layers depicted in FIG. 14 are not meant to limit the amount of sub-layers that can be used as a laminate structure for a particular ultraviolet transparent enclosure. For example, there can be more or less sub-layers in a laminate structure used with an ultraviolet transparent enclosure than that depicted in FIG. 14. Furthermore, it is understood that the order of sub-layers of 106A-106D described with respect to FIG. 14 can vary in their order of arrangement from an outer layer to an inner layer. In addition, the function of the sub-layers can also vary in their use within the laminate.

Figure 15:
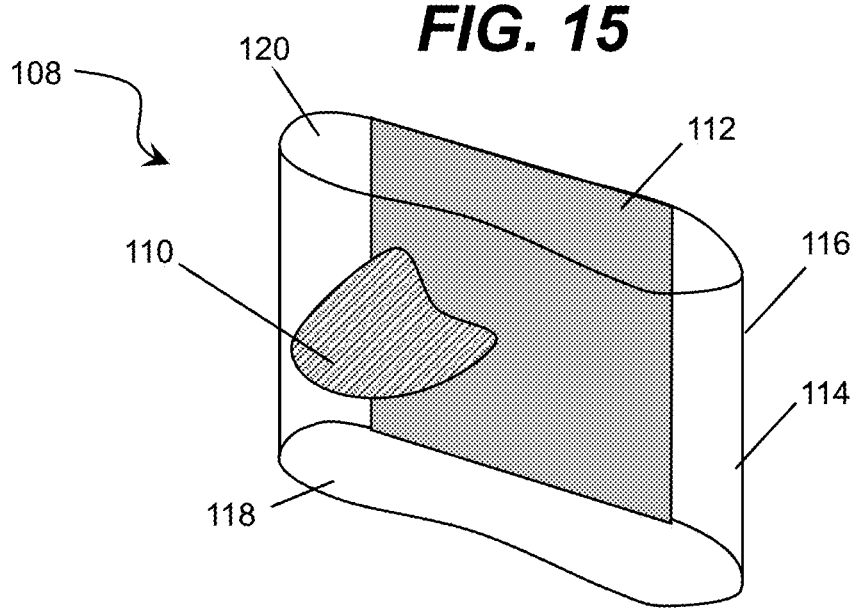
FIG. 15 shows an ultraviolet transparent enclosure having an ultraviolet transparent domain and a reflective domain embedded therein according to an embodiment.

FIG. 15 shows an ultraviolet transparent enclosure 108 having an ultraviolet transparent domain 110 and a reflective domain 112 embedded therein according to an embodiment. As shown in FIG. 15, the ultraviolet transparent enclosure 108 can include several interconnected walls 114 defining side walls 116, a bottom wall 118 and an opening 120. In this manner, the ultraviolet transparent enclosure 108 can be used for disinfecting articles placed within the enclosure. In particular, the enclosure can house medical equipment requiring disinfection, or a liquid requiring UV disinfection.

In one embodiment, the ultraviolet transparent domain 110 can include any of the aforementioned fluoropolymers. In a specific embodiment, the ultraviolet transparent domain 110 can include a fluoropolymer film having $SiO_2$, $Al_2O_3$ and/or the like. In another embodiment, the ultraviolet transparent domain 110 can include a Fresnel lens, or other lens element, or set of elements in order to focus UV radiation onto an article or matter requiring disinfection.

In one embodiment, the reflective domain 112 can include a material that is at least 30% reflective, such as an aluminum film, or a diffusively reflective polymer such as PTFE. In this manner, ultraviolet radiation that is generated by ultraviolet radiation sources (not shown in FIG. 15) is diffusively reflected off of the reflective domain 112 and scattered throughout the ultraviolet transparent enclosure 108.

Figure 16:
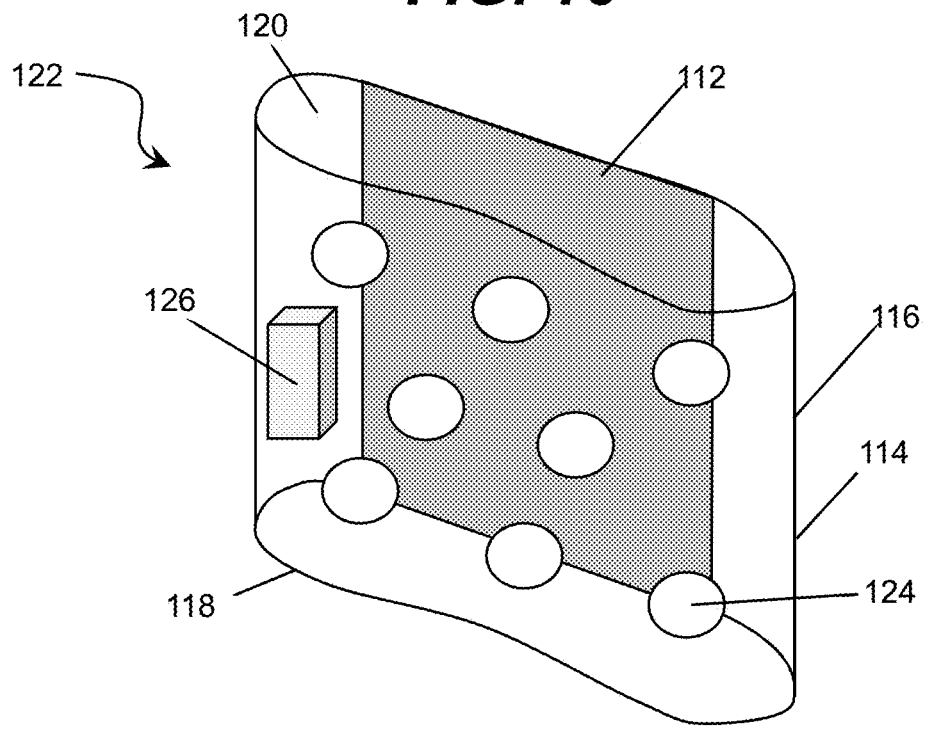
FIG. 16 shows an ultraviolet transparent enclosure having a set of ultraviolet radiation sources and a control unit with electrical components embedded therein according to an embodiment.

FIG. 16 shows an ultraviolet transparent enclosure 122 having ultraviolet radiation sources 124 and a control unit 126 with other electrical components according to an embodiment. The ultraviolet radiation sources 124 can comprise any combination of one or more ultraviolet radiation emitters. For example, the set of ultraviolet radiation sources 124 can include a high intensity ultraviolet lamp (e.g., a high intensity mercury lamp), a discharge lamp, an ultraviolet light emitting diode (LED), super luminescent LEDs, laser diodes, and/or the like. In another embodiment, the set of ultraviolet radiation sources 124 can include a set of light emitting diodes manufactured with one or more layers of materials selected from the group-III nitride material system. Additionally, the set of ultraviolet radiation sources 124 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a plurality of ultraviolet fibers, each of which terminates at an opening, a diffuser, and/or the like.

In one embodiment, the control unit 126 can activate the operation of some or all of the ultraviolet radiation sources 124. Activating the operation of the ultraviolet radiation sources 124 by the control unit 126 can include specifying a plurality of operating parameters that can depend on the use of the ultraviolet transparent enclosure 122 (e.g., disinfection of an article). In one embodiment, the plurality of operating parameters can include a time duration that the ultraviolet radiation sources 124 emits the ultraviolet radiation, a dosage of ultraviolet radiation delivered by the ultraviolet radiation sources 124, a power setting for operating the ultraviolet radiation sources 124, and a maximum operating temperature. It is understood that these operating parameters are illustrative of some of the parameters that can be set by the control unit 126 and is not meant to be limiting as other parameters exist which may need to be specified, such as radiation wavelength, the angular distribution of radiation, and/or the overall spectral power distribution.

In one embodiment, the control unit 126 can operate in conjunction with a multitude of sensors (not shown in FIG. 16) located within and/or about the ultraviolet transparent enclosure 122. A non-exhaustive list of sensors that can be used includes a pressure sensor, a proximity sensor (e.g., a capacitance, optical, magnet proximity sensor), a bacterial fluorescence sensor, a temperature sensor, a chemical sensor, and a radiation sensor.

The sensors, which could be located within the ultraviolet transparent enclosure 122, adhering to its inner surface, could generate signals representative of the conditions that each are configured to detect and send those signals to the control unit 126 for processing and control of any operations that are being performed in the enclosure. For example, a temperature sensor can detect the temperature within the ultraviolet transparent enclosure 122 and/or the temperature of a surface of an object in the enclosure, a chemical sensor can detect a level of a particular chemical that resides on a surface of the object being irradiated with the ultraviolet radiation, and a radiation sensor can detect a level of radiation that is present in the enclosure. It is understood that these sensors can be deployed along with the ultraviolet radiation sources 124 in any desired configuration. For example, the sensors can be interspersed with the ultraviolet radiation sources 124 or separated from each other.

During operation of the ultraviolet radiation sources 124 for a particular operation thereof, the control unit 126 can be used to control at least one of a plurality of predetermined ultraviolet radiation characteristics associated with the ultraviolet radiation emitted from the ultraviolet radiation sources 124. The predetermined ultraviolet radiation characteristics that can be controlled by the control unit 126 can include wavelengths, intensities, and durations and/or the like. In one embodiment, the control unit 126 can control the wavelength of ultraviolet radiation and intensity spatially over a surface of an object being irradiated. As an example, the control unit 126 can control the ultraviolet radiation sources 124 to operate at a target wavelength and intensity for a duration that is designed for the disinfection of bacteria and/or viruses on a surface of an object.

In addition, during an operation, the control unit 126 can be used to turn on or off some or all of the ultraviolet radiation sources 124 dependent upon the detected conditions provided by the sensors. In one embodiment, the control unit 126 can turn on or off each of the ultraviolet radiation sources 124 via an actuator. Also, the control unit can be used to adjust one or more of the ultraviolet radiation characteristics based on the conditions detected by the sensors. For example, the control unit 126 can use the signals from a bacterial fluorescence sensor that are representative of the amount of bacteria, germs, viruses, and the like present on a surface of an object to adjust the intensity, the wavelength, the duration and or the pattern of the ultraviolet radiation emitted from any of the ultraviolet radiation sources 124. In another embodiment, the control unit 126 can be configured to interrupt the operation of the ultraviolet radiation sources 124 in response to receiving temperature signals from a temperature sensor and determining that the temperature has exceeded the maximum temperature. The control unit 126 can then resume the operation after a predetermined cooling time has elapsed.

One of the other electrical components that can be associated with the control unit 126 that can be used with the ultraviolet transparent enclosure 122 can include a timer with switches and/or the like to manage the duration that the ultraviolet radiation sources 124 are on for a particular treatment and ensure that radiation is applied to a particular surface of an object for that duration. In one embodiment, the control unit 126 operating in conjunction with the timer can manage the amount of time that the ultraviolet radiation sources 124 radiate in the UV-C range versus the UV-B range. The duration and frequency treatment that the ultraviolet radiation sources 124 are utilized can depend on detected condition signals provided to the control unit 126 by any of the sensors, as well as any other predetermined factors such as the length that a particular object being irradiated has been used, areas of contact when in use, and whether a set predefined treatment schedule is being followed.

The control unit 126 can also include a wireless transmitter and receiver that is configured to communicate with a remote location via WiFi, BLUETOOTH, and/or the like. As used herein, a remote location is a location that is apart from the ultraviolet transparent enclosure 122. For example, a remote computer can be used to transmit operational instructions to the wireless transmitter and receiver. The operational instructions can be used to program functions performed and managed by the control unit 126. In another embodiment, the wireless transmitter and receiver can transmit operation results, data from the sensors to the remote computer, to facilitate any maintenance and diagnostic operations.

Other electrical components that can operate in conjunction with the control unit 126 can include an input/output component to allow a user to interact with the ultraviolet transparent enclosure, and to receive information therefrom. In one embodiment, the input/output component can permit a user to adjust at least one of the aforementioned plurality of operating parameters. This includes making adjustments during a particular operation and/or prior to initiating a treatment. In one embodiment, the input/output component can include a set of buttons and/or the touch screen on the exterior of the ultraviolet transparent enclosure 122 that enable a user to specify various input selections regarding the operating parameters. In one embodiment, the input/output component can include a visual display for providing status information on an operation (e.g., time remaining, the presence of bacteria, viruses, germs or the like), an indication that a particular operation is recommended, an indication that the object has been sterilized, disinfected, sanitized, an indication that the object has been disinfected, sanitized, an indication after its last use, a simple visual indicator that displays whether an particular operation is underway (e.g., an illuminated light) or if the operation is over (e.g., absence of an illuminated light).

The control unit 126 can further include a power source that is configured to power each of the ultraviolet radiation sources 124, the control unit and any sensors. In one embodiment, the power source can take the form of one or more batteries, solar cells, a vibration power generator that can generate power based on magnetic inducted oscillations or stresses developed on a piezoelectric crystal. In another embodiment, the power source can include a super capacitor that is rechargeable. Other power components that are suitable for use as the power source can include a mechanical energy to electrical energy converter such as a piezoelectric crystal, and a rechargeable device.

Figure 17:
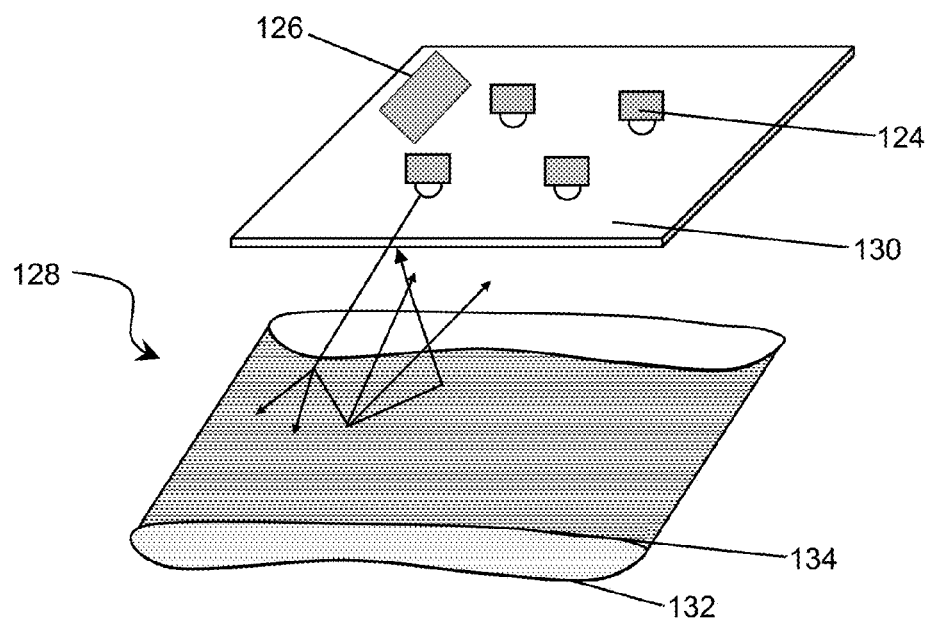
FIG. 17 shows an ultraviolet transparent enclosure having an ultraviolet module of ultraviolet radiation sources that is detachable from the enclosure according to an embodiment.

Although FIG. 16 shows the ultraviolet radiation sources 124 and the control unit 126 integrated with the ultraviolet transparent enclosure 122, it is possible to have these components configured as an ultraviolet module that is detachable from the enclosure. For example, FIG. 17 shows an ultraviolet transparent enclosure 128 having an ultraviolet module 130 including the ultraviolet radiation sources 124 and the control unit 126 that is detachable from the enclosure according to an embodiment. In one embodiment, the ultraviolet module 130 includes a flexible substrate that supports the set of ultraviolet radiation sources 124 and the control unit 126. Examples of a flexible substrate that can support the set of ultraviolet radiation sources 124 and the control unit 126 within the ultraviolet transparent enclosure 128 can comprise a flexible polymer, a flexible metalo-polymer composite, or rubber based substrate. In each of these examples of a flexible substrate, all material could incorporate all of the necessary electronics, input and output devices for supporting and operating the set of ultraviolet radiation sources 124 and the control unit 126.

In one embodiment, the ultraviolet module 130 with the set of ultraviolet radiation sources 124 and the control unit 126 can be positioned above ultraviolet transparent enclosure 128 which can have an ultraviolet reflective surface 132 and ultraviolet transparent surface 134. In this manner, the ultraviolet reflective surface 132 can reflect back the ultraviolet light generated from the ultraviolet radiation sources 124 causing the circulation of the radiation within the ultraviolet transparent enclosure 128. In one embodiment, the ultraviolet reflective surface 132 can include, but is not limited to, aluminum films, or reflective polymers such as GORE® or PTFE. In one embodiment, the ultraviolet transparent surface 134 can include, but is not limited to, fluoropolymers, and or UV transparent oxides such as $Al_2O_3$ or $SiO_2$. In one embodiment, the ultraviolet transparent surface 134 can include an ultraviolet diffusively transparent material that includes, but is not limited to, TEFLON®, EFEP, and/or the like. In order to attain further circulation of the ultraviolet light between the ultraviolet module 130 and the ultraviolet reflective surface 132, the module can comprise an ultraviolet reflective surface that includes any of the material described herein. This enables one to increase the ultraviolet dose within the ultraviolet transparent enclosure 128.

It is understood that the placement of the ultraviolet module 130 is not meant to be limited to placement above the ultraviolet transparent enclosure 128 as depicted in FIG. 17, and those skilled in the art will appreciate that many other configurations are possible. For example, the ultraviolet module 130 can be placed within the ultraviolet transparent enclosure 128 and can be physically removed and inserted as desired. In this manner, the ultraviolet transparent enclosure 128 is suited for applications that can include, but is not limited to, disinfection of articles or materials.

Figure 18:
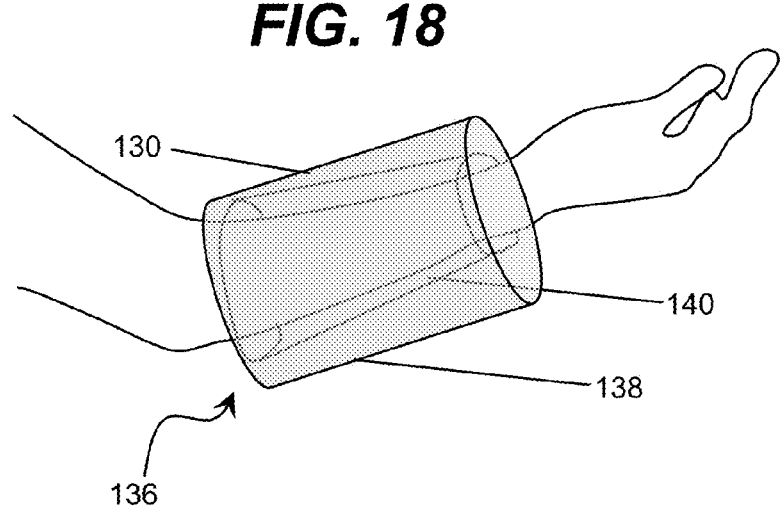
FIG. 18 shows an ultraviolet transparent enclosure with a flexible ultraviolet module that is wrapped around an object for disinfection according to an embodiment.

FIG. 18 shows an ultraviolet transparent enclosure 136 that includes a flexible ultraviolet module 130 with the flexible substrate that can support the set of ultraviolet radiation sources 124 and the control unit 126. In this manner, the ultraviolet transparent enclosure 136 with the flexible ultraviolet module 130 can be wrapped around an object for disinfection according to an embodiment. For clarity, the ultraviolet module 130 depicted in FIG. 18 does not show the set of ultraviolet radiation sources 124 and the control unit 126. In one embodiment, as shown in FIG. 18, the ultraviolet transparent enclosure 136 with the ultraviolet module 130 can be used in a medical treatment of a patient. However, it is understood that the ultraviolet transparent enclosure 136 with the ultraviolet module 130 is suitable for any application in an industrial, a business or an educational setting in which an article or object may have a need for a disinfection treatment. The use of the ultraviolet transparent enclosure 136 in any one of these settings will depend on several factors that can include, but is not limited to, the size and shape of the article or object and how easily that it can be wrapped or covered by the enclosure.

In the example depicted in FIG. 18, in which the ultraviolet transparent enclosure 136 with the ultraviolet module 130 is used in a medical treatment, the enclosure can be wrapped around a portion of a patient's body, such as the patient's arm 138. In one embodiment, the ultraviolet transparent enclosure 136 can have an ultraviolet transparent face 140 that can receive ultraviolet radiation directed from ultraviolet radiation sources such as those present in the ultraviolet module 130. In this manner, continuing with the arm as an illustrative portion of a patient's body being treated, the ultraviolet radiation generated from the ultraviolet radiation sources can be directed to the patient's arm to perform a disinfection treatment of the arm. In another embodiment, the ultraviolet transparent enclosure 136 can include a type of medicine that can be administered to the patient's arm upon being wrapped there around. Examples of medicine that are suitable for application to a patient's arm in a wrapped medium can include, but is not limited to, topical anti-inflammatory medicines, antibiotics, and ointments for burns, cuts, scrapes and the like.

Figure 19:
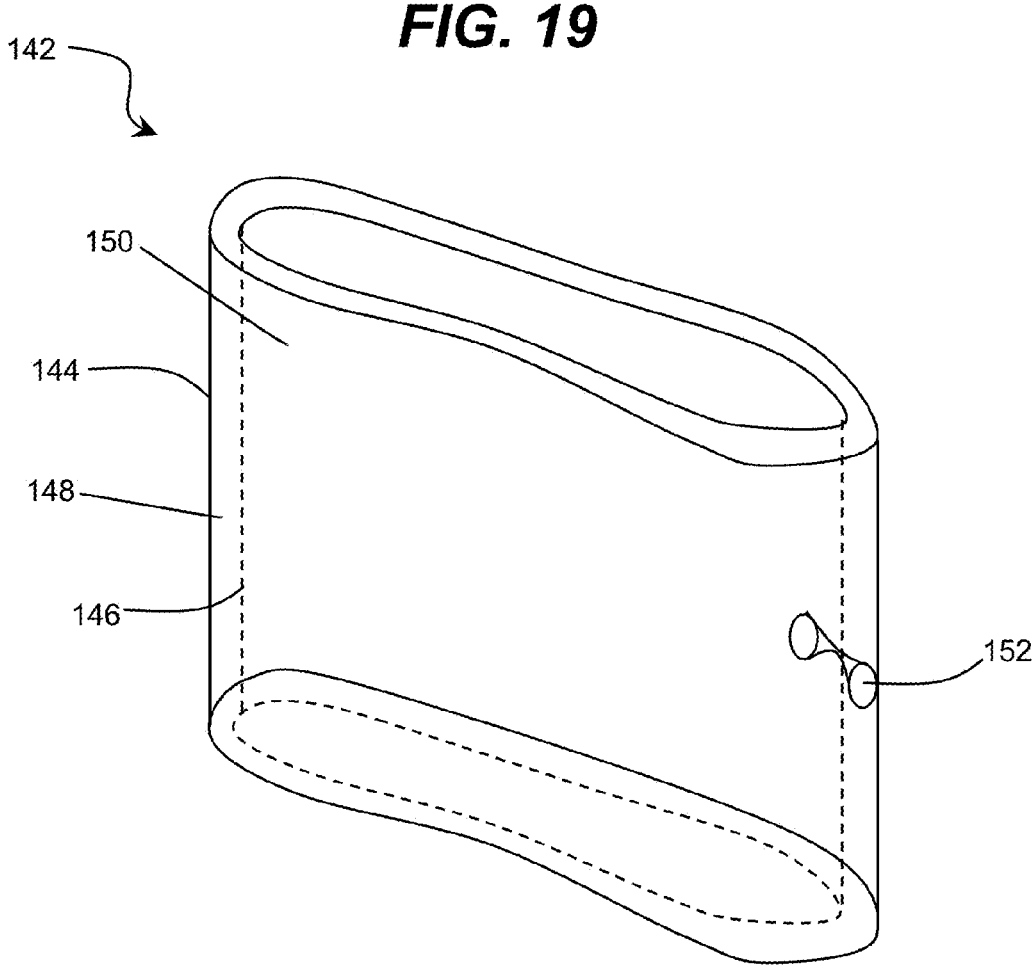
FIG. 19 shows an ultraviolet transparent enclosure having interconnected ultraviolet transparent walls according to an embodiment.

FIG. 19 shows an ultraviolet transparent enclosure 142 having a multiple of interconnected ultraviolet transparent walls according to an embodiment. Like the ultraviolet transparent enclosure 136 of FIG. 18, the ultraviolet transparent enclosure 142 of FIG. 19 can include the flexible ultraviolet module 130, which makes it suited for medical applications as well as other uses in which an object or article that is in need of a disinfection, and that can be wrapped with and/or covered by the enclosure.

In one embodiment, the ultraviolet transparent enclosure 142 can include an outer wall 144 and an inner wall 146. Both the outer wall 144 and the inner wall 146 can be made from any of the fluoropolymers described herein. The outer wall 144 and the inner wall 146 that form the ultraviolet transparent enclosure 142 can be formed as a unitary construction or as separate walls that are interconnected. In one embodiment, the outer wall 144 and the inner wall 146 of the ultraviolet transparent enclosure 142 can define one or a pair of openings to insert an extremity, an object or an article there through. In this manner, the ultraviolet transparent enclosure 142 can be used as a sleeve-like enclosure as opposed to an enclosure that is wrapped around an extremity, an object or an article.

In one embodiment, the outer wall 144 and the inner wall 146 of the ultraviolet transparent enclosure 142 can be separated from each other by an ultraviolet transparent transmission medium 148. For example, the ultraviolet transparent transmission medium 148 can include space between the walls that can be filled with a medium that can include, but is not limited to, air, gas, ultraviolet transparent medicine, or water. In an embodiment, the ultraviolet transparent transmission medium 148 can include a medicine that is activated by ultraviolet radiation applied to the ultraviolet transparent enclosure 142 via an ultraviolet module or ultraviolet radiation sources that are external to the enclosure. In one embodiment, the inner wall 146 can contain micro pores for allowing medicine to penetrate the inner portion of a cavity 150 formed within the ultraviolet transparent enclosure 142. Alternatively, the cavity 150 of the ultraviolet transparent enclosure 142 can be completely isolated from the ultraviolet transparent transmission medium 148 between the outer wall 144 and the inner wall 146.

As shown in FIG. 19, the outer wall 144 and the inner wall 146 can be connected by interconnection domains 152. Note that for clarity, the ultraviolet transparent enclosure 142 can include more than one domain. In one embodiment, the interconnection domains 152 can be formed from a plastic material, such as for example, any of the fluoropolymers described herein. In this manner, the interconnection domains 152 can be used to provide structural stability for the ultraviolet transparent enclosure 142. In another embodiment, in which the ultraviolet transparent enclosure 142 is used for medical applications, the interconnection domains 152 can be configured with an input port and an output port for supplying medicine and/or accessing items from within the enclosure (e.g., tissue or biopsy samples taken from an extremity of a patient).

Figure 20:
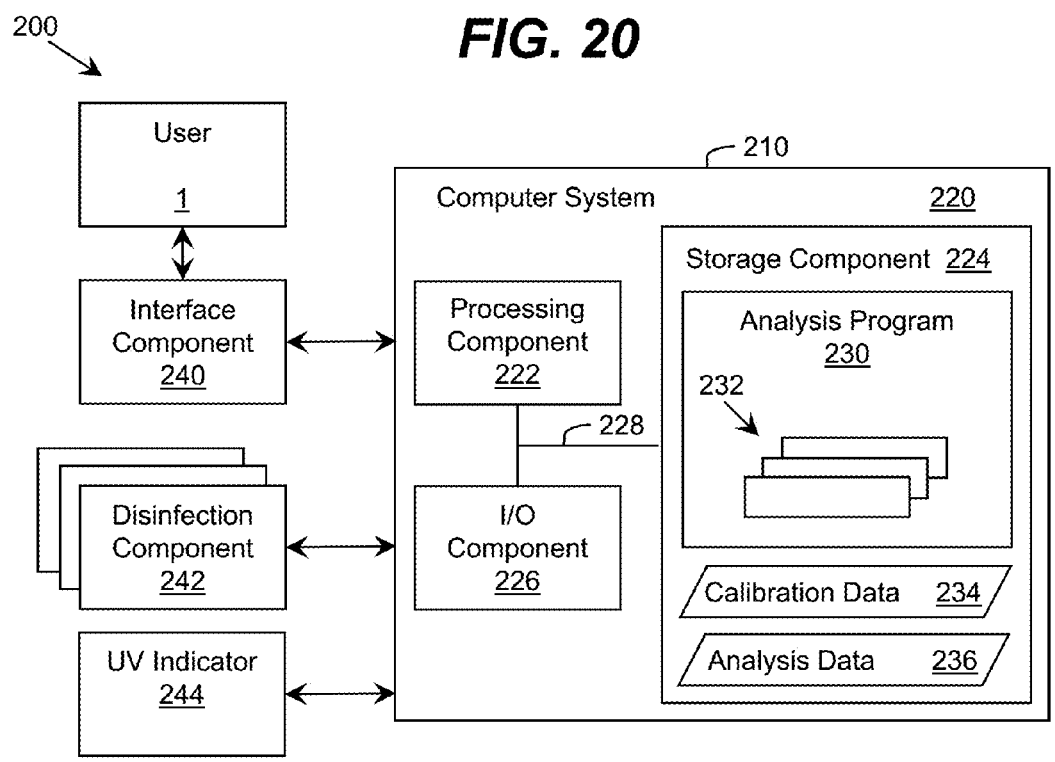
FIG. 20 shows an illustrative disinfection system according to an embodiment.

FIG. 20 shows an illustrative disinfection system 200 according to an embodiment that is suitable to operate in conjunction with any of the various ultraviolet transparent enclosures described herein. In this case, the system 200 includes a monitoring and/or control component 210, which is implemented as a computer system 220 including an analysis program 230, which makes the computer system 220 operable to manage a set of disinfection components 242 (e.g., a power component, ultraviolet (UV) source(s), sensor(s), valves, etc.) by performing a process described herein. In particular, the analysis program 230 can enable the computer system 220 to operate the disinfection components 242 and process data corresponding to one or more conditions of the disinfection components and/or the media to be disinfected (e.g., transparency of the media).

In an embodiment, during an initial period of operation, the computer system 220 can acquire data regarding one or more attributes of the fluid and generate analysis data 236 for further processing. The analysis data 236 can include information on the presence of one or more contaminants in the fluid, an article, an object, an extremity, a transparency of the fluid/article/object/extremity, and/or the like. The computer system 220 can use the analysis data 236 to generate calibration data 234 for controlling one or more aspects of the operation of the disinfection components 242 by the computer system 221 as discussed herein.

The computer system 220 is shown including a processing component 222 (e.g., one or more processors), a storage component 224 (e.g., a storage hierarchy), an input/output (I/O) component 226 (e.g., one or more I/O interfaces and/or devices), and a communications pathway 228. In general, the processing component 222 executes program code, such as the analysis program 230, which is at least partially fixed in the storage component 224. While executing program code, the processing component 222 can process data, which can result in reading and/or writing transformed data from/to the storage component 224 and/or the I/O component 226 for further processing. The pathway 228 provides a communications link between each of the components in the computer system 220. The I/O component 226 and/or the interface component 227 can comprise one or more human I/O devices, which enable a human user 1 to interact with the computer system 220 and/or one or more communications devices to enable a system user 1 to communicate with the computer system 220 using any type of communications link. To this extent, during execution by the computer system 220, the analysis program 230 can manage a set of interfaces (e.g., graphical user interface(s), application program interface, and/or the like) that enable human and/or system users 1 to interact with the analysis program 230. Furthermore, the analysis program 230 can manage (e.g., store, retrieve, create, manipulate, organize, present, etc.) the data, such as calibration data 234 and analysis data 236, using any solution. A UV indicator 244 can provide a visible and/or audible indicator (e.g., light, sound, and/or the like) to indicate that ultraviolet radiation is being generated.

In any event, the computer system 220 can comprise one or more general purpose computing articles of manufacture (e.g., computing devices) capable of executing program code, such as the analysis program 230, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 230 can be embodied as any combination of system software and/or application software.

Furthermore, the analysis program 230 can be implemented using a set of modules 232. In this case, a module 232 can enable the computer system 220 to perform a set of tasks used by the analysis program 230, and can be separately developed and/or implemented apart from other portions of the analysis program 230. When the computer system 220 comprises multiple computing devices, each computing device can have only a portion of the analysis program 230 fixed thereon (e.g., one or more modules 232). However, it is understood that the computer system 220 and the analysis program 230 are only representative of various possible equivalent monitoring and/or control systems 210 that may perform a process described herein. To this extent, in other embodiments, the functionality provided by the computer system 220 and the analysis program 230 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 210 can be implemented without any computing device, e.g., using a closed loop circuit implementing a feedback control loop in which the outputs of one or more disinfection components 242 (e.g., sensing devices) are used as inputs to control the operation of one or more other disinfection components 242 (e.g., UV LEDs).

Regardless, when the computer system 220 includes multiple computing devices, the computing devices can communicate over any type of communications link. Furthermore, while performing a process described herein, the computer system 220 can communicate with one or more other computer systems, such as the user 1, using any type of communications link. In either case, the communications link can comprise any combination of various types of wired and/or wireless links; comprise any combination of one or more types of networks; and/or utilize any combination of various types of transmission techniques and protocols.

While shown and described herein as a method and system for treating (e.g., disinfecting) a fluid, an article, object, extremity, and/or the like, it is understood that aspects of the invention further provide various alternative embodiments. For example, in one embodiment, the invention provides a computer program fixed in at least one computer-readable medium, which when executed, enables a computer system to treat a fluid as described herein. To this extent, the computer-readable medium includes program code, such as the analysis program 230, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 230, which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for disinfecting a media (e.g., fluid, colloid, mixture, an article, an object, an extremity, and/or the like). In this case, the generating can include configuring the computer system 220 to implement the method of treating a fluid, an article, an object, an extremity, and/or the like, as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An apparatus, comprising:
an ultraviolet transparent enclosure including an inlet to receive a flow of media entering the ultraviolet transparent enclosure for disinfection and an outlet to supply the flow of media from the ultraviolet transparent enclosure after disinfection, wherein the ultraviolet transparent enclosure includes a plurality of spaced media separators, each contacting only one side surface of the ultraviolet transparent enclosure, wherein adjacent media separators each contact an opposing side surface, the plurality of spaced media separators forming a channel that twists and turns the flow of media from the inlet to the outlet, and wherein the ultraviolet transparent enclosure includes a material that prevents biofouling from accumulating therein; and a set of ultraviolet radiation sources, located adjacent to the ultraviolet transparent enclosure, to generate ultraviolet radiation towards the ultraviolet transparent enclosure.

2. The apparatus of claim 1, wherein the plurality of spaced media separators are arranged vertically within the ultraviolet transparent enclosure.

3. The apparatus of claim 2, wherein the inlet and the outlet are located at opposing end faces of the ultraviolet transparent enclosure, and wherein the set of ultraviolet radiation sources includes a first set of ultraviolet radiation sources oriented at an end face of the ultraviolet transparent enclosure having the inlet and a second set of ultraviolet radiation sources oriented at an opposing end face of the ultraviolet transparent enclosure having the outlet.

4. The apparatus of claim 1, wherein the plurality of spaced media separators are arranged horizontally within the ultraviolet transparent enclosure.

5. The apparatus of claim 4, wherein the inlet and the outlet are located at one of the side surfaces of the ultraviolet transparent enclosure that have contact with the plurality of media separators, and wherein the set of ultraviolet radiation sources are proximate an end face of the ultraviolet transparent enclosure and oriented perpendicularly to the plurality of media separators.

6. The apparatus of claim 1, further comprising a reflective enclosure that encases the ultraviolet transparent enclosure.

7. The apparatus of claim 6, wherein the set of ultraviolet radiation sources are integrated within the reflective enclosure.

8. The apparatus of claim 7, wherein the reflective enclosure includes a plurality of reflecting mirrors, each located within a path of ultraviolet radiation generated from one of the ultraviolet radiation sources.

9. An apparatus, comprising:
an ultraviolet transparent enclosure including an inlet to receive a flow of media entering the ultraviolet transparent enclosure for disinfection and an outlet to supply the flow of media from the ultraviolet transparent enclosure after disinfection, wherein the ultraviolet transparent enclosure includes a material that prevents biofouling from accumulating therein;
a reflective enclosure that encases the ultraviolet transparent enclosure; and
an illuminator integrated within an inner surface of the reflective enclosure, wherein the illuminator comprises a set of ultraviolet radiation sources positioned to generate ultraviolet radiation towards the ultraviolet transparent enclosure.

10. The apparatus of claim 9, wherein the illuminator includes a top surface, a bottom surface and a pair of opposing side surfaces, wherein the top surface and the pair of opposing side surfaces are highly reflective to the ultraviolet radiation and the bottom surface is transparent to the ultraviolet radiation.

11. The apparatus of claim 10, wherein the set of ultraviolet radiation sources are oriented to direct the ultraviolet radiation to at least one of the top surface and the pair of opposing side surfaces.

12. The apparatus of claim 9, wherein the set of ultraviolet radiation sources comprise at least two distinct sources having at least two distinct peak emission wavelengths separated by at least a full width at half maximum.

13. An apparatus, comprising:
an ultraviolet transparent enclosure including an inlet and an outlet for a flow of media to be disinfected, wherein the ultraviolet transparent enclosure includes a material having a laminate of sublayers that are configured to prevent biofouling within the ultraviolet transparent enclosure; and
a set of ultraviolet radiation sources located adjacent to the ultraviolet transparent enclosure, the set of ultraviolet radiation sources configured to generate ultraviolet radiation towards the ultraviolet transparent enclosure.

14. The apparatus of claim 13, wherein the laminate of sublayers includes at least one sublayer having ultraviolet diffusive properties.

15. The apparatus of claim 13, wherein the laminate of sublayers includes at least one sublayer having ultraviolet fluorescence.

16. The apparatus of claim 13, wherein the laminate of sublayers includes at least one sublayer having reflective properties over a fraction of a surface area of the sublayer.

17. The apparatus of claim 13, wherein the laminate of sublayers includes at least one sublayer having anti-biofouling properties, wherein an inner sublayer includes the anti-biofouling properties.

18. The apparatus of claim 13, further comprising an ultraviolet module that is detachable from the ultraviolet transparent enclosure, wherein the ultraviolet module includes a flexible substrate that supports the set of ultraviolet radiation sources.

19. The apparatus of claim 13, wherein the ultraviolet transparent enclosure includes a plurality of interconnected walls, wherein some of the interconnected walls are separated from each other by an ultraviolet transparent transmission medium.

20. The apparatus of claim 13, wherein the ultraviolet transparent enclosure is a flexible module adapted to wrap around an object that is to be subjected to disinfection.

* * * * *